US009169291B2

(12) United States Patent
Sasaki et al.

(10) Patent No.: US 9,169,291 B2
(45) Date of Patent: *Oct. 27, 2015

(54) COVALENT CONJUGATES BETWEEN ENDOPEROXIDES AND TRANSFERRIN AND LACTOFERRIN RECEPTOR-BINDING AGENTS

(75) Inventors: Tomikazu Sasaki, Bothell, WA (US); Henry Chiu-Yuen Lai, Seattle, WA (US); Narendra Pal Singh, Lynnwood, WA (US); Steve J. Oh, Mill Creek, WA (US)

(73) Assignee: University of Washington, Seattle, WA (US)

(*) Notice: Subject to any disclaimer, the term of this patent is extended or adjusted under 35 U.S.C. 154(b) by 1259 days.

This patent is subject to a terminal disclaimer.

(21) Appl. No.: 13/027,112

(22) Filed: Feb. 14, 2011

(65) Prior Publication Data
US 2011/0150830 A1    Jun. 23, 2011

Related U.S. Application Data

(62) Division of application No. 11/692,866, filed on Mar. 28, 2007, now abandoned.

(60) Provisional application No. 60/743,851, filed on Mar. 28, 2006.

(51) Int. Cl.
*C07K 7/08* (2006.01)
*C07K 7/02* (2006.01)
*A61K 38/04* (2006.01)
*A61K 47/48* (2006.01)
*B82Y 5/00* (2011.01)
*C07D 493/18* (2006.01)
*C07D 493/20* (2006.01)
*C07D 519/00* (2006.01)
*C07K 7/06* (2006.01)
*A61K 38/00* (2006.01)

(52) U.S. Cl.
CPC ............. *C07K 7/08* (2013.01); *A61K 47/48246* (2013.01); *A61K 47/48346* (2013.01); *B82Y 5/00* (2013.01); *C07D 493/18* (2013.01); *C07D 493/20* (2013.01); *C07D 519/00* (2013.01); *C07K 7/06* (2013.01); *A61K 38/00* (2013.01)

(58) Field of Classification Search
None
See application file for complete search history.

(56) References Cited

U.S. PATENT DOCUMENTS

| 4,978,676 | A | 12/1990 | Thornfeldt | |
|---|---|---|---|---|
| 5,057,501 | A | 10/1991 | Thornfeldt | |
| 5,180,840 | A | 1/1993 | Avery | |
| 5,216,175 | A | 6/1993 | Avery | |
| 5,219,880 | A | 6/1993 | Thornfeldt | |
| 5,225,427 | A | 7/1993 | Venugopalan | |
| 5,225,437 | A | 7/1993 | Posner | |
| 5,578,637 | A | 11/1996 | Lai | |
| 6,486,199 | B1 | 11/2002 | Vennerstrom | |
| 6,743,893 | B2 * | 6/2004 | Engler et al. | 530/300 |
| 6,906,205 | B2 | 6/2005 | Vennerstrom | |
| 7,371,778 | B2 | 5/2008 | Vennerstrom | |
| 7,417,156 | B2 | 8/2008 | Posner | |
| 8,048,850 | B2 * | 11/2011 | Lai et al. | 514/1.3 |
| 2004/0058981 | A1 | 3/2004 | Lai | |
| 2004/0067875 | A1 | 4/2004 | Lai | |
| 2006/0193778 | A1 | 8/2006 | Engler | |

FOREIGN PATENT DOCUMENTS

| WO | 97/01548 A1 | 1/1997 |
|---|---|---|
| WO | 99/33461 A1 | 7/1999 |
| WO | 00/42046 A1 | 7/2000 |

OTHER PUBLICATIONS

Li, 2005, Expert Opin. Ther. Targets, 9(5):995-1007.*
Anfosso, L., et al., "Microarray Expression Profiles of Angiogenesis-Related Genes Predict Tumor Cell Response to Artemisinins," Pharmacogenomics Journal 6(4):269-278, Jul.-Aug. 2006.
Asawamahasakda, W., et al., "Reaction of Antimalarial Endoperoxides With Specific Parasite Proteins," Antimicrobial Agents and Chemotherapy 38(8):1854-1858, Aug. 1994.
Avery, M.A., et al., "The Total Synthesis of (+)-Artemisinin and (+)-9-Desmethylartemisinin," Tetrahedron Letters 28(40):4629-4632, Sep. 1987.
Benoit-Vical, F., et al., "In Vitro and In Vivo Potentiation of Artemisinin and Synthetic Endoperoxide Antimalarial Drugs by Metalloporphyrins," Antimicrobial Agents and Chemotherapy 44(10):2836-2841, Oct. 2000.
Berger, T.G., et al., "Artesunate in the Treatment of Metastatic Uveal Melanoma—First Experiences," Oncology Reports 14(6):1599-1603, Dec. 2005.
Bez, G., et al., "Recent Developments With 1,2,4-Trioxane-Type Artemisinin Analogues," Current Organic Chemistry 7(12):1231-1255, 2003.
Bjerrum, E.J., et al., "Design, Synthesis, and Pharmacology of a Highly Subtype Selective GluR1/2 Agonist, (RS)-2-Amino-3-(4-chloro-3-hydroxy-5-isoxazolyl)propionic Acid (Cl-HIBO)," Journal of Medicinal Chemistry 46(11):2246-2249, May 2003.
Cabanes, D., et al., "Surface Proteins and the Pathogenic Potential of *Listeria monocytogenes*," Trends in Microbiology 10(5):238-245, May 2002.
Chen, X., et al., "Synthesis and Biological Evaluation of Dimeric RGD Peptide-Paclitaxel Conjugate as a Model for Integrin-Targeted Drug Delivery," Journal of Medicinal Chemistry 48(4):1098-1106, Feb. 2005.
Cornelissen, C.N., "Transferrin-Iron Uptake by Gram-Negative Bacteria," Frontiers in Bioscience 8:d836-847, May 2003.

(Continued)

*Primary Examiner* — Satyanarayana R Gudibande
(74) *Attorney, Agent, or Firm* — Christensen O'Connor Johnson Kindness PLLC

(57) ABSTRACT

The invention relates to covalent conjugates between endoperoxides and small peptides and organic compounds that bind to molecular cavities on the transferrin or lactoferrin receptor, and the use of compositions comprising these conjugates to treat cancer, hyperproliferative disorders, inflammatory diseases, and infections.

5 Claims, 5 Drawing Sheets

(56) References Cited

OTHER PUBLICATIONS

Cumming, J.N., et al., "Design, Synthesis, Derivatization, and Structure—Activity Relationships of Simplified, Tricyclic, 1,2,4-Trioxane Alcohol Analogues of the Antimalarial Artemisinin," Journal of Medicinal Chemistry 41(6):952-964, Mar. 1998.

Davis, R.J., et al., "Insulin-Like Growth Factor I and Epidermal Growth Factor Regulate the Expression of Transferrin Receptors at the Cell Surface by Distinct Mechanisms," Journal of Biological Chemistry 262(27):13126-13134, Sep. 1987.

Davis, R.J., et al., "Insulin Stimulates Cellular Iron Uptake and Causes the Redistribution of Intracellular Transferrin Receptors to the Plasma Membrane," Journal of Biological Chemistry 261(19):8708-8711, Jul. 1986.

Dawson, M.I., et al., "Aromatic Retinoic Acid Analogues. 2. Synthesis and Pharmacological Activity," Journal of Medicinal Chemistry 26(9):1282-1293, Sep. 1983.

Disbrow, G.L., et al., "Dihydroartemisinin is Cytotoxic to Papillomavirus-Expressing Epithelial Cells In Vitro and In Vivo," Cancer Research 65(23):10854-10861, Dec. 2005.

Efferth, T., et al., "Activity of Drugs From Traditional Chinese Medicine Toward Sensitive and MDR1- or MRP1-Overexpressing Multidrug-Resistant Human CCRF-CEM Leukemia Cells," Blood Cells, Molecules, and Diseases 28(2):160-168, Mar.-Apr. 2002.

Efferth, T., et al., "The Anti Malarial Artesunate is Also Active Against Cancer," International Journal of Oncology 18(4):767-773, Apr. 2001.

Efferth, T., et al., "Enhancement of Cytotoxicity of Artemisinins Toward Cancer Cells by Ferrous Iron," Free Radical Biology & Medicine 37(7):998-1009, Oct. 2004.

Efferth, T., et al., "mRNA Expression Profiles for the Response of Human Tumor Cell Lines to the Antimalarial Drugs Artesunate, Arteether, and Artemether," Biochemical Pharmacology 64(4):617-623, Aug. 2002.

Evans, R.W., and J.S. Oakhill, "Transferrin-Mediated Iron Acquisition by Pathogenic *Neisseria*," Biochemical Society Transactions 30(4):705-707, Aug. 2002.

Faul, M.M., et al., "Synthesis of Novel Retinoid X Receptor-Selective Retinoids," Journal of Organic Chemistry 66(17):5722-5782, Aug. 2001.

Gray-Owen, S.D., and A.B. Schryvers, "Bacterial Transferrin and Lactoferrin Receptors," Trends in Microbiology 4(5):185-191, May 1996.

Gu, H.-M., et al., "Antimalarial Activities of 25 Derivatives of Artemisinine Against Chloroquine-Resistant *Plasmodium berghei*," Acta Pharmacologica Sinica 1(1):48-50, Sep. 1980.

Hull, K.G., et al., "Synthesis of Ro 25/8210 Via an Enantioselective Oxazaborolidine-Catalyzed Reduction," Tetrahedron 53(37):12405-12414, Sep. 1997.

Husson, M. O., et al., "Iron Acquisition by *Helicobacter* pylori: Importance of Human Lactoferrin," Infection and Immunity 61(6):2694-2697, Jun. 1993.

Imakura, Y., et al., "Acid Degradation Products of Qinghaosu and Their Structure—Activity Relationships," Heterocycles 31(6):1011-1016, Jun. 1990.

Imakura, Y., et al., "Synthesis of Desethanoqinghaosu, a Novel Analogue of the Antimalarial Qinghaosu," Journal of the Chemical Society, Chemical Communications 5:372-374, Mar. 1988.

Kim, B.J., and T. Sasaki, "Synthesis of O-Aminodihydroartemisinin Via TMS Inflate Catalyzed C—O Coupling Reaction," Journal of Organic Chemistry 69(9):3242-3244, Apr. 2004.

Kuo, G. H., et al., "Synthesis and Discovery of Macrocyclic Polyoxygenated Bis-7-azaindolylmaleimides as a Novel Series of Potent and Highly Selective Glycogen Synthase Kinase-3β Inhibitors," Journal of Medicinal Chemistry 46(19):4021-4031, Sep. 2003.

Lai, H., and N.P. Singh, "Selective Cancer Cell Cytotoxicity From Exposure to Dihydroartemisinin and Holotransferrin," Cancer Letters 91(1):41-46, May 1995.

Lai, H., et al., "Effects of Artemisinin-Tagged Holotransferrin on Cancer Cells," Life Sciences 76(11):1267-1279, Jan. 2005.

Lai, H., et al., "Targeted Treatment of Cancer With Artemisinin and Artemisinin-Tagged Iron-Carrying Compounds," Expert Opinion on Therapeutic Targets 9(5):995-1007, Oct. 2005 (abstract only).

Lee, J.H., et al., "Receptor Mediated Uptake of Peptides That Bind the Human Transferrin Receptor," European Journal of Biochemistry 268(7):2004-2012, Apr. 2001.

Li, Y. et al "Novel Antitumor Artemisinin Derivatives Targeting G1 Phase of the Cell Cycle," Bioorganic & Medicinal Chemistry Letters 11(1):5-8, Jan. 2001.

Lim, B.C., et al., "Transferrin-Receptor Interaction and Iron Uptake by Reticulocytes of Vertebrate Animals—A Comparative Study," Journal of Comparative Physiology B 157(3):363-371, 1987.

Martin, V.J.J., et al., "Engineering a Mevalonate Pathway in *Escherichia coli* for Production of Terpenoids," Nature Biotechnology 21(7):796-802, Jul. 2003.

Mazmanian, S.K., et al., "Passage of Heme-Iron Across the Envelope of *Staphylococcus aureus*," Science 299(5608):906-909, Feb. 2003.

Moore, J.C., et al., "Oral Administration of Dihydroartemisinin and Ferrous Sulfate Retarded Implanted Fibrosarcoma Growth in the Rat," Cancer Letters 98(1):83-87, Nov. 1995.

Nilsson, J.W., et al., "Synthesis and SAR of Thrombin Inhibitors Incorporating a Novel 4-Amino-Morpholinone Scaffold: Analysis of X-Ray Crystal Structure of Enzyme Inhibitor Complex," Journal of Medicinal Chemistry 46(19):3985-4001, Sep. 2003.

Olakanmi, O., et al., "The Nature of Extracellular Iron Influences Iron Acquisition by *Mycobacterium* tuberculosis Residing Within Human Macrophages," Infection and Immunity 72(4):2022-2028, Apr. 2004.

Palermo, L.M., et al., "Residues in the Apical Domain of the Feline and Canine Transferrin Receptors Control Host-Specific Binding and Cell Infection of Canine and Feline Parvoviruses," Journal of Virology 77(16):8915-8923, Aug. 2003.

Peters, W., et al., "The Chemotherapy of Rodent Malaria. XLIX. The Activities of Some Synthetic 1,2,4-Trioxanes Against Chloroquine-Sensitive and Chloroquine-Resistant Parasites. Part 2: Structure—Activity Studies on cis-Fused Cyclopenteno-1,2,4-trioxanes (fenozans) Against Drug-Sensitive and Drug-Resistant Lines of *Plasmodium berghei* and *P. yoelii* ssp. NS In Vivo," Annals of Tropical Medicine and Parasitology 87(1):9-16, Feb. 1993.

Posner, G.H., et al., "Orally Active, Antimalarial, Anticancer, Artemisinin-Derived Trioxane Dimers With High Stability and Efficacy," Journal of Medicinal Chemistry 46(6):1060-1065, Mar. 2003.

Posner, G.H., et al., "Orally Active, Hydrolytically Stable, Semisynthetic, Antimalarial Trioxanes in the Artemisinin Family," Journal of Medicinal Chemistry 42(2):300-304, Jan. 1999.

Qian, Z.M., et al., "Targeted Drug Delivery Via the Transferrin Receptor-Mediated Endocytosis Pathway," Pharmacological Reviews 54(4):561-587, Dec. 2002.

Raimundo, B.C., et al., "Integrating Fragment Assembly and Biophysical Methods in the Chemical Advancement of Small-Molecule Antagonists of IL-2: An Approach for Inhibiting Protein-Protein Interactions," Journal of Medicinal Chemistry 47(12):3111-3130, Jun. 2004.

Sadava, D., et al., "Transferrin Overcomes Drug Resistance to Artemisinin in Human Small-Cell Lung Carcinoma Cells," Cancer Letters 179(2):151-156, May 2002.

Singh, N.P., and H. Lai, "Selective Toxicity of Dihydroartemisinin and Holotransferrin Toward Human Breast Cancer Cells," Life Sciences 70(1):49-56, Nov. 2001.

Singh, N.P., and K.B. Verma, "Case Report of a Laryngeal Squamous Cell Carcinoma Treated With Artesunate," Archive of Oncology 10(4):279-280, Dec. 2002.

Singh, N.P., and V.K. Panwar, "Case Report of a Pituitary Macroadenoma Treated With Artemether," Integrative Cancer Therapies 5(4)391-394, Dec. 2006.

Terng, H.-J., et al., "Human Transferrin Receptor is Active and Plasma Membrane-Targeted in Yeast," FEMS Microbiology Letters 160(1):61-67, Mar. 1998.

Thumshirn, G., et al., "Multimeric Cyclic RGD Peptides as Potential Tools for Tumor Targeting: Solid-Phase Peptide Synthesis and Chemoselective Oxime Ligation," Chemistry: A European Journal 9(12):2717-2725, Jun. 2003.

(56) References Cited

OTHER PUBLICATIONS

Tsypin, G.I., et al., "Structure and Reactivity of Aliphatic Azido Compounds. VIII. Isomeric Composition of the Products From Cycloaddition of Aliphatic Azides to Acetylene Derivatives," translated from Zhurnal Organicheskoi Khimii (Russian Journal of Organic Chemistry) 13(11):2275-2281, Nov. 1977.

Van Bockxmeer, F.M., and E.H. Morgan, "Comparative Aspects of Transferrin-Reticulocyte Interactions: Membrane Receptors and Iron Uptake," Comparative Biochemistry and Physiology. Part A: Physiology 71(2):211-218, 1982.

Vennerstrom, J.L., and J.W. Eaton, "Oxidants, Oxidant Drugs, and Malaria," Journal of Medicinal Chemistry 31(7):1269-1277, Jul. 1988.

Vennerstrom, J.L., et al., "Dispiro-1,2,4,5-tetraoxanes: A New Class of Antimalarial Peroxides," Journal of Medicinal Chemistry 35(16):3023-3027, Aug. 1992.

Vennerstrom, J.L., et al., "Identification of an Antimalarial Synthetic Trioxolane Drug Development Candidate," Nature 430(7002):900-904, Aug. 2004.

Wandersman, C., and I. Stojiljkovic, "Bacterial Heme Sources: The Role of Heme, Hemoprotein Receptors and Hemophores," Current Opinion in Microbiology 3(2):215-220, Apr. 2000.

Woerdenbag, H.J., et al., "Cytotoxicity of Artemisinin-Related Endoperoxides to Ehrlich Ascites Tumor Cells," Journal of Natural Products 56(6):849-856, Jun. 1993.

Wu, J. M., et al., "Synthesis and Cytotoxicity of Artemisinin Derivatives Containing Cyanoarylmethyl Group," European Journal of Medicinal Chemistry 36(5):469-479, May 2001.

Wu, T.Y.H., et al., "Development and Characterization of Nonpeptidic Small Molecule Inhibitors of the XIAP/Caspase-3 Interaction," Chemistry & Biology 10(8):759-767, Aug. 2003.

Xia, H., et al., "Recombinant Human Adenovirus: Targeting to the Human Transferrin Receptor Improves Gene Transfer to Brain Microcapillary Endothelium," Journal of Virology 74(23):11359-11366, Dec. 2000.

Zaman, S.S., and R.P. Sharma, "Some Aspects of the Chemistry and Biological Activity of Artemisinin and Related Antimalarials," Heterocycles 32(8):1593-1638, 1991.

Zhang, Y., et al., "Identification of the Receptor Binding Domain of the Mouse Mammary Tumor Virus Envelope Protein," Journal of Virology 77(19):10468-10478, Oct. 2003.

\* cited by examiner

COVALENT CONJUGATES BETWEEN ENDOPEROXIDES AND TRANSFERRIN AND LACTOFERRIN RECEPTOR-BINDING AGENTS

CROSS-REFERENCES TO RELATED APPLICATIONS

This application is a division of U.S. patent application Ser. No. 11/692,866, filed Mar. 28, 2007, which claims the benefit of U.S. Provisional Application No. 60/743,851, filed Mar. 28, 2006, both of which applications are expressly incorporated herein by reference.

FIELD OF THE INVENTION

The invention relates to covalent conjugates between endoperoxides and small peptides and organic compounds that bind to molecular cavities on the transferrin or lactoferrin receptor, and the use of compositions comprising these conjugates to treat cancer, hyperproliferative disorders, inflammatory diseases, and infections.

BACKGROUND OF THE INVENTION

Artemisinin, isolated from the plant *Artemisia annua* L., is a sesquiterpene lactone which contains an endoperoxide bridge that reacts with an iron atom to form free radicals. Plant extracts containing artemisinin have been used to treat malaria for over 1600 years. The anti-malarial action of this compound is due to its reaction with intra-parasitic heme iron to generate free radicals, causing cell death. Since cancer cells are known to have a significantly higher influx of iron than normal cells, many studies have shown that artemisinin and its analogs are cytotoxic against established tumors and tumor cell lines (see, e.g., Woerdenbag et al. (1993) *J. Nat. Prod.* 56(6):849-856; Lai and Singh (1995) *Cancer Lett.* 91:41-46; Efferth et al. (2001) *Int. J. Oncol.* 18:767-773; Li et al. (2001) *Bioorg. Med. Chem. Lett.* 11:5-8; Singh and Lai (2001) *Life Sci.* 70:49-56; Efferth et al. (2002) *Biochem. Pharmacol.* 64:617-623; Efferth et al. (2002) *Blood Cells, Molecules and Diseases* 28(2):160-168; Sadava et al. (2002) *Cancer Lett.* 179:151-156; Berger et al. (2005) *Oncol. Rep.* 14:1599-1603; Disbrow et al. (2005) *Cancer Res.* 65:10854-10861).

Many analogs of artemisinin and other compounds containing an endoperoxide bridge that are biologically active have been described (see, e.g., U.S. Pat. No. 5,180,840; U.S. Pat. No. 5,216,175; U.S. Pat. No. 5,225,427; Cumming et al. (1998) *J. Med. Chem.* 41(6):952-964; Posner et al. (1999) *J. Med. Chem.* 42:300-304; Li et al. (2001) *Bioorg. Med. Chem. Lett.* 11:5-8; Wu et al. (2001) *Eur. J. Med. Chem.* 36:469-479; Posner et al. (2003) *J. Med Chem* 46:1060-5; Vennerstrom et al. (2004) *Nature* 430:900-904). Analogs of artemisinin that have been used in the treatment of malaria include dihydroartemisinin, artemether, artesunate, arteether, propylcarbonate dihydroartemisinin and artelinic acid.

Artemisinin is a relatively safe drug, with few and minor side effects even at high doses. Oral doses of 70 mg/kg/day for 6 days, for example, have been used in humans to treat malaria. No apparent adverse side effects were observed when a cancer patient was treated with artesunate for a period of 9 months (intramuscular dose of 60 mg/day for 15 days; oral dose of 50 mg per day for 8.5 months) (Singh and Verma (2002) *Arch. Oncol.* 10(4):279-280). A patient with pituitary macroadenoma was also treated orally with artemether for a period of 12 months, without any observed adverse side effects (Singh and Panwar (2006) Integr Cancer Ther. 5(4): 391-4). Artemisinin and artemisinin analogs have also been used in the treatment of skin conditions such as psoriasis, blistering skin diseases, viral warts, mulluscum contagiosum, and hemorrhoids (see, e.g., U.S. Pat. No. 4,978,676; U.S. Pat. No. 5,219,880). U.S. Pat. No. 5,057,501 discloses the use of combinations artemisinin and artemisinin analogs with monocarboxylic acids, esters or amides in the treatment of papulosquamous skin diseases, including psoriasis, and eczematous skin diseases, including seborrheic and atopic dermatitis. The administration of iron salts or the iron-carrying protein holotransferrin increases the susceptibility of cancer cells and implanted tumors to artemisinin and its analogs (Lai and Singh (1995) *Cancer Lett.* 91:41-46; Moore et al. (1995) *Cancer Lett.* 98:83-87; Singh and Lai (2001) *Life Sci.* 70:49-56; Sadava et al. (2002) *Cancer Lett.* 1179:151-156; Efferth et al. (2004) *Free Radic. Biol. Med.* 37:998-1009).

Several pathogens obtain iron from iron-carrying host proteins. *Neisseria meningitidis*, the causative agent of bacterial meningitis, for example, expresses cell surface receptors for host iron-carrying compounds such as transferrin and lactoferrin (Evans and Oakhill (2002) *Biochem. Soc. Trans.* 30(4): 705-707). No vaccine is currently available for the B strain of *N. meningitidis*, the most prevalent strain in the Western world. *Helicobacter pylori*, the etiologic agent of gastritis, gastric and duodenal ulcers, and adenocarcinoma in humans, also obtains iron by binding human lactoferrin (Husson et al. (1993) *Infect. Immun.* 61(6):2694-2697). Fungi are also known to obtain iron from host iron-carrying proteins (Terng et al. (1998) *FEMS Microbiol. Lett.* 160:61-67).

U.S. Pat. No. 5,225,427 discloses 10-substituted ether derivatives of dihydroartemisinin alleged to exhibit antimalarial and antiprotozoal activity.

U.S. Pat. No. 5,578,637 discloses methods of killing cancer cells wherein compounds having an endoperoxide moiety that is reactive with heme are administered under conditions that enhance intracellular iron concentrations. Endoperoxide bearing sesquiterpene including artemisinin and its analogs are preferred compounds.

U.S. Patent Application No. 2004/0058981 discloses methods for preventing or delaying the development of cancer by administering free radical-generating agents to a subject. Preferred compounds include endoperoxide bearing sesquiterpene compounds such as artemisinin and its analogs. Intracellular iron concentrations may be enhanced by the administration of iron salts or complexes.

U.S. Patent Application No. 2004/0067875 discloses covalent conjugates between artemisinin-related endoperoxides and iron-carrying proteins, such as holotransferrin, to treat cancer and infections by pathogens that bind iron-carrying proteins.

U.S. Patent Application No. 2006/0193778 and U.S. Pat. No. 6,743,893 disclose peptides discovered by phage display techniques that are capable of binding to and internalizing with the human transferring receptor, including the peptides HAIYPRH (SEQ ID NO: 1) and THRPPMWSPVWP (SEQ ID NO: 2).

U.S. Patent Application No. 2006/0142377 discloses orally active artemisinin-derived trioxane dimers suitable as orally active compounds, which demonstrate antimalarial and anti-tumor activities.

There is a need in the art for artemisinin compositions with increased efficacy for the treatment of cancer and disease caused by pathogens that interact with receptors for iron-carrying host proteins. There is also a need for methods for treating cancer and infections caused by pathogens that obtain iron by internalizing or using iron from iron-carrying host proteins. The present invention addresses these needs.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

The invention relates to covalent conjugates between endoperoxides and small peptides and organic compounds that bind to molecular cavities on the transferrin or lactoferrin receptor, and the use of compositions comprising these conjugates to treat cancer, hyperproliferative disorders, inflammatory diseases, and infections.

One embodiment of the invention includes compounds comprising at least one endoperoxide containing moiety covalently linked to a receptor binding agent that binds to a transferrin receptor or a lactoferrin receptor on a cell without interfering with transferrin or lactoferrin binding to the same receptor.

Another embodiment includes compositions comprising a compound comprising at least one endoperoxide containing moiety covalently linked to a receptor binding agent that binds to a transferrin receptor or a lactoferrin receptor on a cell without interfering with transferrin or lactoferrin binding to the same receptor, and a pharmaceutically acceptable carrier.

Another embodiment of the invention includes a method of treating a disease or condition elected from the group consisting of cancer; restenosis; proliferative eye, kidney, and skin diseases; precancerous hyperplastic conditions, e.g., benign prostatic hyperplasia (BPH) and benign breast disease (BBD); autoimmune disease; arthritis; graft rejection; inflammatory bowel disease; proliferation induced after medical procedures; an infection by a pathogenic organism that has a receptor for an iron-carrying protein selected from the group consisting of transferrin and lactoferrin; topical bacterial infections; gingivitis; skin infections; and eye infections; comprising administering to said subject an effective amount of a composition comprising a compound comprising at least one endoperoxide containing moiety covalently linked to a receptor binding agent that binds to a transferrin receptor or a lactoferrin receptor on a cell without interfering with transferrin or lactoferrin binding to the receptor.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE INVENTION

Figure 1:
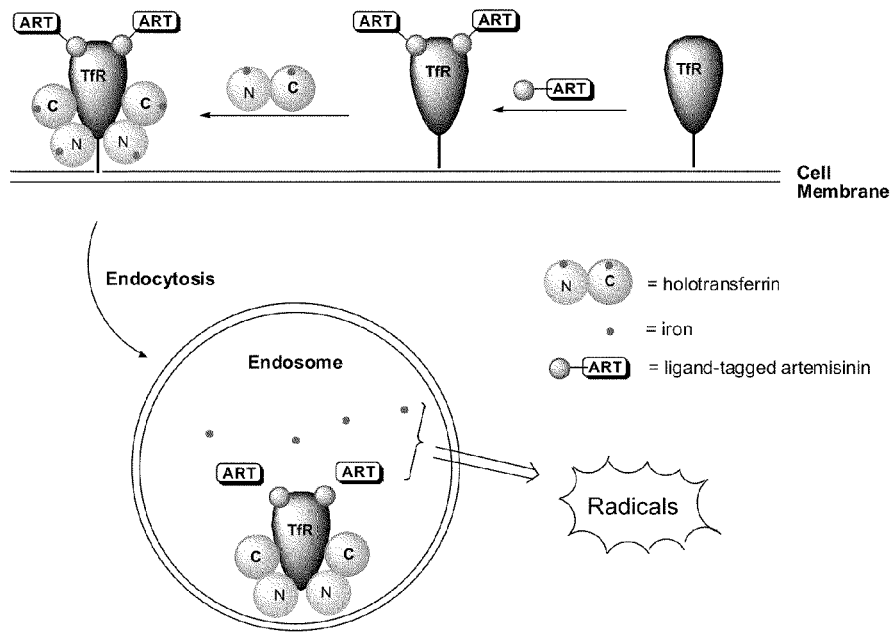
FIG. 1 shows a schematic diagram for transferrin receptor-targeted delivery of artemisinin.

The invention relates to covalent conjugates between endoperoxides and small peptides and organic compounds that bind to molecular cavities on the transferrin or lactoferrin receptor, and the use of compositions comprising these conjugates to treat cancer, hyperproliferative disorders, inflammatory diseases, and infections.

One aspect of the invention includes compounds comprising at least one endoperoxide containing moiety covalently linked to a receptor binding agent that binds to a transferrin receptor or a lactoferrin receptor on a cell without interfering with transferrin or lactoferrin binding to the same receptor.

As used herein, the term "covalent conjugate" refers to a compound in which an endoperoxide is covalently linked to small peptides and organic compounds that bind to molecular cavities on the transferrin or lactoferrin receptor.

The term "endoperoxide" refers to a compound having an endoperoxide bridge, which can react with an iron atom to form free radicals, causing cell death. Endoperoxide compounds may also form free radicals in the presence of copper and manganese. The source of endoperoxides may be natural (e.g., isolated from plants), synthetic, or semi-synthetic. For example, the free radical-generating agents may be produced by expressing the enzymes for the relevant synthetic pathways in a microbial host (see, e.g., Martin et al. (2003) *Nature Biotechnol.* 21:796-802). Representative endoperoxides are set forth herein, although it will be apparent that other endoperoxides will be useful for this purpose.

Another aspect of the invention provides covalent conjugates wherein the endoperoxide containing moiety comprises an endoperoxide bridge. The key "core structure" conveying activity to the compounds and conjugates of the invention is the endoperoxide bridge defined by 1,2,4-trioxane and 1,2,4,5-tetraoxane derivatives. The term "artemisinin-related endoperoxide compounds" encompasses both 1,2,4-trioxane and 1,2,4,5-tetraoxane derivatives, as described more fully below.

One aspect of the invention provides covalent conjugates between endoperoxides and transferrin receptor-binding agents. In some embodiments, the endoperoxide is selected from the group consisting of sesquiterpene lactones and alcohols, carbonates, esters, ethers, and sulfonates thereof, arteflene, 1,2,4-trioxanes, and 1,2,4,5-tetraoxanes.

The endoperoxide may have the structure:

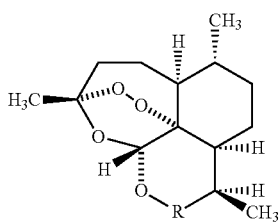

wherein R is

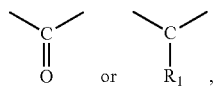

where $R_1$ is hydrogen, hydroxyl, alkyl, or has the formula:

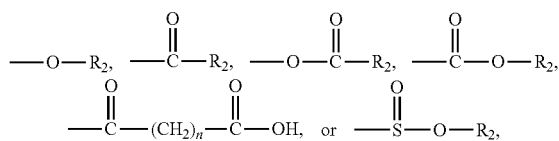

where $R_2$ is alkyl or aryl and n is 1 to 6, and the pharmaceutically acceptable salts thereof. As used herein, the term "alkyl" means lower alkyl having from 1 to 6 carbon atoms, preferably 1 to 4 carbon atoms. Alkyl groups of the invention may be straight-chain or branched-chain groups. The term "aryl" refers to monocyclic and polycyclic aromatic groups containing from 4 to 14 backbone carbon or heteroatoms, and includes both carbocyclic aryl groups and heterocyclic aryl groups. Carbocyclic aryl groups are aryl groups in which all ring atoms are carbon. Heterocyclic aryl groups have from 1 to 4 heteroatoms as ring atoms with the remainder of the ring atoms being carbon. Representative aryl groups include, for example, phenyl and benzyl. Pharmaceutically acceptable salts include the alkali or alkaline earth metal salts, preferably sodium or potassium.

Artemisinin, a highly oxygenated sesquiterpene lactone endoperoxide isolated by Chinese researchers in 1971, has been found to be a plasmocidal and blood schizontocidal agent superior to conventional antimalarial drugs against malarial strains. Artemisinin-related endoperoxides include artemisinin, where R is

dihydroartemisinin ($R_1$=—OH), artesunic acid ($R_1$=—OCO(CH$_2$)$_2$CO$_2$H), and artesunate, artemether ($R_1$=—OCH$_3$), and arteether ($R_1$=—OC$_2$H$_5$). Other representative endoperoxide compounds included in the definition of artemisinin-related endoperoxides include artelinic acid, dihydroartemisinin propyl carbonate, arteflene (Ro. 42-1611) and its analogs (Biirgen et al. (1994) *Sixth Int. Cong. Infect. Dis. Abst.* 427, p. 152, Prague), 1,2,4-trioxanes (Peters et al. (1993) *Ann. Trop. Med. Parasit.* 87(1):9-16) and 1,2,4,5-tetraoxanes (Vennerstrom et al. (1992) *J. Med. Chem.* 35(16): 3023-3027). Other suitable structural analogs of artemisinin are described in, for example, U.S. Pat. Nos. 5,216,175 and 5,180,840; Cumming et al. (1998) *J. Med. Chem.* 41(6):952-964; and PCT patent applications WO 97/01548, WO 99/33461, and WO 00/42046.

The artemisinin molecule and related compounds have been studied by many by different groups covering aspects such as characterization, total synthesis, and understanding of the mechanism of action through QSAR studies. These studies have unveiled a large amount of information about this artemisinin and related endoperoxide compounds and have resulted in a large number of published and patented literatures (See, Bez, G., et al., *Current Organic Chemistry* 7:1231-1255, 2003). For example, the endoperoxide function has been shown to be essential for the antimalarial activity antimalarial activity of artemisinin (Gu, *Acta Pharmacol. Sinica* 1(1):48-50, 1980 Abstract). The total synthesis of (+)-artemisinin has been reported (Avery, M. A., et al., *Tetrahedron Letters* 28:4629-4632, 1987). The same group also synthesized several simplified analogues of artemisinin (Avery, 1987). Desethanoqinghaosu has also been (Imakura, Y., et al., *J. Chem. Soc. Chem. Comm.,* 1988, pp. 372-374). Lin et al. reported a new series of hydrolytically stable and water-soluble dihydroartemisinin derivatives with optically active side chains as potential antimalarial agents. (Lin, 1989) Imakura et al. reported the study of acid degradation products of Qinghaosu and their structure-activity relationships (Imakura, Y., et al., *Heterocycles* 31(6):1011-1016, Jun. 1, 1990. Abstract). Zaman et al. reported the aspects of the chemistry and biological activity of artemisinin and related antimalarials. (Zaman, S. S., and R. P. Sharma, *Heterocycles* 32:1593-1638, 1991). Peters et al. evaluated the activities of some synthetic artemisinin endoperoxide 1,2,4-trioxanes against several lines of *Plasmodium berghei* and *P. yoelii* ssp. NS in vivo. (Peters, W., et al., *Ann. Trop. Med. Parasit.* 87(1): 9-16, 1993). The results from these studies have enabled scientists during the 1990s to delineate the basic structural requirement for artemisinin-related 1,2,4-trioxane endoperoxides—the 1,2,4-trioxane ring system—as the essential pharmacophore for artemisinin. Since then, interest in artemisinin has persisted. Benoit-Vical et al. reported the in vitro and in vivo potentiation of artemisinin and synthetic endoperoxide antimalarial drugs in 2000 (Benoit-Vical, F., et al., *Antimicrobial Agents and Chemotherapy* 44(10):2836-2841, 2000). Recently, Anfosso et al. used microarray expression profiles of angiogenesis-related genes to predict tumor cell response to artemisinin. (Anfosso, L. et al., *Pharmacogenomics Journal,* 2006, pp. 1-10).

The compounds of the invention are not meant to be limited by the specific means of covalently linking the one or more endoperoxide containing moieties to the receptor binding agent that binds to a transferrin receptor or a lactoferrin receptor on a cell without interfering with transferrin or lactoferrin binding to the receptor. Representative linking groups include, for example, those such as covalent bonds, alkylene, arylene, —O—, —CO—, —OCO—, —CO—$(CH_2)$—, —CO—$(CH_2)_n$—CO—, —CO—$(CH_2)_n$—COO—, —CO—$(CH_2)_n$—SOO—, —O-Ph-CONH—, —O-Ph-CONH—N-Ph-CONH—, —O—$CH_2$-Ph-CO—NH—N=CH-Ph-CO—, —O-Ph-CONH—, -Ph-CONH—N-Ph-CONH—, —$CH_2$-Ph-CO—NH—N=CH-Ph-CO—, —O-Ph-CONH—, —O-Ph-CONH—N-Ph-CONH—, and —O—$CH_2$-Ph-CO—NH—N=CH-Ph-CO—. Branched (double amino) amino acids such as lysine, beta-lysine, gamma-lysine, asparagine, arginine, and the like, can be used to facilitate the synthesis of covalent conjugates comprising two or more endoperoxide moieties linked to a single transferrin lactoferrin receptor binding agent, as described above. Other branched linking groups will permit the synthesis of compounds comprising one or more endoperoxide moieties linked to two or more transferrin or lactoferrin receptor binding agents.

As a result of an apparent association between the endoperoxide functional group and antimalarial activity, a substantial effort has been devoted to developing new peroxide antimalarials (Vennerstrom, J. L., and J. W. Eaton, *Journal of Medicinal Chemistry* 31(7):1269-1277, 1988). Motivated by the structure and pharmacological mechanism of artemisinin, a large number of molecules containing mainly the core pharmacophore, 1,2,4-trioxane, as well as its close analogue, 1,2,4,5-tetraoxane, and other endoperoxides have been synthesized and studied (U.S. Pat. No. 6,906,205, U.S. Pat. No. 6,486,199). Rational design of structurally simpler analogs of artemisinin has led to the synthesis of various racemic 1,2,4-trioxanes displaying potent antimalarial activities (U.S. Pat. No. 5,225,437) Another group reported the development of dispiro-1,2,4,5-tetraoxanes as endoperoxide antimalarial drugs (Vennerstrom, J. L., et al., *Journal of Medicinal Chemistry* 35:3023-3027, 1992), as well as identification of a series of 1,2,4-trioxolane antimalarial drug candidates (US 2005/0256185).

1,2,4-Trioxane itself has not been isolated or characterized. The tremendous amount of literature in the field suggests that it is the discovery of artemisinin with its novel 1,2,4-trioxane heterocyclic pharmacophore that initiated the development of 1,2,4-trioxanes, 1,2,4,5-tetraoxanes, and other artemisinin-related endoperoxides derivatives. Therefore, it would be readily apparent to a person of ordinary skill in the art that the term "artemisinin-related endoperoxide compounds" encompasses both 1,2,4-trioxane and 1,2,4,5-tetraoxane derivatives.

Because artemisinin reacts with intra-parasitic heme through its endoperoxide bridge to generate free radicals and cause cell death, and because cancer cells have a significantly higher influx of iron than normal cells, it has been shown that artemisinin and artemisinin analogs are cytotoxic against established tumors and tumor cells lines. Many analogs of artemisinin and other compounds containing an endoperoxide bridge (see, e.g., U.S. Pat. No. 5,216,175) are useful in treating several varieties of diseases. U.S. Pat. No. 5,216,175 also discloses many 1,2,4-trioxanes.

The term "artemisinin-related endoperoxide" is defined as a compound having an endoperoxide bridge, which reacts with an iron atom to form free radicals, causing cell death. The application further indicates that the artemisinin-related endoperoxide "is selected from the group consisting of sesquiterpene lactones and alcohols, carbonates, esters, ethers, and sulfonates thereof, arteflene, 1,2,4-trioxanes, and 1,2,4,5-tetraoxanes."

Representative endoperoxide compounds of the invention include 1,2,4-trioxanes (Peters et al., (1993) *Ann. Trop. Med. Parasit.* 87(1):9-16) and 1,2,4,5-tetraoxanes (Vennerstrom et al. (1992) *J. Med. Chem.* 35(16):3023-3027).

An ideal requirement for cancer chemotherapy is that the therapeutic agent acts specifically on cancer cells, with little toxicity towards normal cells. Artemisinin has been shown to have relatively high selectivity on cancer cells, e.g., it has a therapeutic index (i.e., toxicity towards cancer cells versus that on normal cells) of approximately 100 on human leukemia cells. This is due to cancer cells picking up and containing a high concentration of iron that reacts with artemisinin and other artemisinin-related endoperoxides. Iron converts endoperoxides into free radicals that kill cells. Covalently tagging artemisinin-related endoperoxides to the iron-carrying protein transferrin increases the cancer cell cytotoxicity of the artemisinin-related endoperoxides by approximately 2 fold and cancer/normal cell selectivity by 950 fold (Lai et al. (2005) *Life Sci.* 76:1267-79). Since cancer cells, in general, have a high cell surface concentration of transferrin receptors that uptake transferrin, tagging of artemisinin-related endoperoxides to transferrin provides selective delivery of these endoperoxides to cancer cells. Iron is released from transferrin intracellularly and reacts immediately with the tagged endoperoxide, causing cell death. Methods for targeting the delivery of drugs by the transferrin receptor-mediated endocytosis pathway have been reviewed (Qian et al. (2002) *Pharmacological Rev* 54: 561-587).

A variety of cancers are known to be associated with elevated transferrin receptor expression. Table 1, shown below, provides a summary of literature references, grouped by cancer type.

TABLE 1

| Cancers with Elevated Transferrin Receptor Expression |
| --- |
| Liver Cancer and Hepatitis C |
| Sciot R et al., Histopathology 1988 January; 12(1): 53-63. |
| Lee A W, Oates P S, Trinder D. Hepatology 2003 October; 38(4): 967-77. |
| Pascale R M et al., Hepatology 1998 February; 27(2): 452-61. |
| Lin J. Zhonghua Yi Xue Za Zhi 1992 February; 72(2): 86-7, 128. |
| Sciot R, Van Eyken P, Desmet V J. Histopathology 1990 January; 16(1): 59-62. |
| Bolewska B et al., Pol Merkur Lekarski 2005 May; 18(107): 552-5. |
| Saito H et al., Hepatol Res 2005 April; 31(4): 203-10. |
| Pancreatic Cancer |
| Buchler M W et al., Eur J Cancer 2004 June; 40(9): 1418-22. |
| Breast Cancer |
| Wrba F et al. Virchows Arch A Pathol Anat Histopathol 1986; 410(1): 69-73. |
| Hogemann-Savellano D et al., Neoplasia 2003 November-December; 5(6): 495-506. |
| Yang D C et al., Anticancer Res 2001 May-June; 21(3B): 1777-87. |

TABLE 1-continued

Cancers with Elevated Transferrin Receptor Expression

Yang D C et al., Anticancer Res 2001 January-February; 21(1B): 541-9.
Cavanaugh P G et al., Breast Cancer Res Treat 1999 August; 56(3): 203-17.
Lung Cancer Anabousi S et al., Eur J Pharm Sci 2006 December; 29(5): 367-74. Epub 2006 Jul. 22.
Dowlati A et al., Br J Cancer 1997; 75(12): 1802-6.
Carbognani P et al., Cancer 1996 Jul. 1; 78(1): 178-9.
Whitney J F et al., Cancer. 1995 Jul. 1; 76(1): 20-5.
Kayser K, Ernst M, Bubenzer J. Exp Pathol 1991; 41(1): 37-43.
Kondo K et al., Chest 1990 June; 97(6): 1367-71.
Vostrejs M et al., J Clin Invest 1988 July; 82(1): 331-9.
Gastric Cancer Yuan P X, Si L S. Zhonghua Bing Li Xue Za Zhi 1992 April; 21(2): 88-91.
Iinuma H et al., Int J Cancer 2002 May 1; 99(1): 130-7.
Colorectal Cancer Brookes M J et al, Gut 2006 October; 55(10): 1449-60. Epub 2006 Apr. 26
Prutki M et al., Cancer Lett 2006 Jul. 18; 238(2): 188-96. Epub 2005 Aug. 18.
Leukemia Shackelford R E et al., Med Hypotheses 2006; 66(3): 509-12. Epub 2005 Dec. 2.
Smilevska T et al., Leuk Res 2006 February; 30(2): 183-9. Epub 2005 Jul. 28.
Staber P B et al., Oncogene 2004 Jan. 29; 23(4): 94-904.
Huang G et al., Hua Xi Yi Ke Da Xue Xue Bao 1997 March; 28(1): 55-7.
Petrini M et al, Cancer Res 1989 Dec. 15; 49(24 Pt 1): 6989-96.
Barnett D et al., Clin Lab Haematol 1987; 9(4): 361-70.
Cervical Cancer Disbrow G L et al, Cancer Res 2005 Dec. 1; 65(23): 10854-61.
Farley J et al., Anal Quant Cytol Histol 1998 August; 20(4): 238-49.
Ovarian Cancer Hereiz H A, Bayoumi F A. J Egypt Public Health Assoc 1992; 67(5-6): 697-707.
Lloyd J M et al., J Clin Pathol 1984 February; 37(2): 131-5.
Brain Cancer Ucar T, Gurer I. Br J Neurosurg 2003 December; 17(6): 525-9.
Wen D Y et al., Neurosurgery 1995 June; 36(6): 1158-63; discussion 1163-4.
Martell L A et al., Cancer Res 1993 Mar. 15; 53(6): 1348-53.
Prior R et al. Virchows Arch A Pathol Anat Histopathol 1990; 416(6): 491-6.
Hall W A et al., J Neurosurg 1992 May; 76(5): 838-44.
Non-Hodgkin's Lymphoma Nejmeddine F et al. J Nucl Med 1999 January; 40(1): 40-5.
Das Gupta A, Shah V I. Hematol Pathol 1990; 4(1): 37-41.
Head and Neck Cancer Kearsley J H et al. Br J Cancer 1990 June; 61(6): 821-7.
Barresi G, Tuccari G. Pathol Res Pract 1987 June; 182(3): 344-51.
Pituitary Cancer Tampanaru-Sarmesiu A et al. Am J Pathol 1998 February; 152(2): 413-22.
Oral Cancer Miyamoto T et al. Int J Oral Maxillofac Surg 1994 December; 23(6 Pt 2): 430-3.
Miyamoto T. Kokubyo Gakkai Zasshi 1992 March; 59(1): 21-32.
Tanaka N et al. Bull Tokyo Med Dent Univ 1991 September; 38(3): 19-26.
Bladder Cancer Limas C. J Pathol 1993 September; 171(1): 39-47.
Smith N W et al., Br J Urol 1990 April; 65(4): 339-44.
Seymour G J et al., Urol Res 1987; 15(6): 341-4.
Melanoma van Muijen G N et al. Int J Cancer 1991 Apr. 22; 48(1): 85-91.
Soyer H P et al. J Cutan Pathol 1987 February; 14(1): 1-5.
Iwata M et al., J Dermatol 1988 June; 15(3): 208-11.
Richardson D R. Biochim Biophys Acta 1991 Feb. 19; 1091(3): 294-302.
Prostate Cancer Keer H N et al., J Urol 1990 February; 143(2): 381-5.
Sahoo S K et al., Int J Cancer. 2004 Nov. 1; 112(2): 335-40.
Rossi M C, Zetter B R. Proc Natl Acad Sci USA 1992 Jul. 1; 89(13): 6197-201.
Biliary Cancer Tuccari G et al., Histol Histopathol 1997 July; 12(3): 671-6.

Artemisinin-related endoperoxide-tagged transferrin has to compete with endogenous transferrin for transferrin receptor binding, which requires administration of sufficient amounts of artemisin-related endoperoxide-tagged transferrin to obtain binding to the transferrin receptor. To circumvent the need to compete with transferrin, the present invention provides covalent conjugates between endoperoxides and transferrin receptor-binding agents. The term "transferrin receptor-binding agents" refers to small peptides and organic compounds that bind to molecular cavities on a receptor for a host iron-carrying compound such as transferrin or lactoferrin. In the covalent conjugates of the invention, endoperoxides are linked to the transferrin receptor-binding agents in any way that preserves both the receptor binding affinity of the transferrin receptor-binding agents and the activity of the endoperoxide. Moreover, the covalent conjugates of the invention do not interfere with transferrin binding to the same transferrin receptor.

The structure of the transferrin-transferrin receptor complex is known. Using the software program called PASS, a number of surface cavities on the transferrin receptor have been identified. When all the cavities that are close to the transferrin-binding site are removed, there are 15 surface cavities ("target cavities") per monomer that could be used to bind the covalent conjugates of the invention. Since the receptor is a symmetric dimer, a total of 30 cavities are available for binding to artemisinin derivatives. Table 2 lists the atomic coordinates of these cavities on the surface of the B-chain of human transferrin receptor. The atomic coordinates are calculated by using the structure of transferrin-transferrin receptor complex (1SUV) that is available from Protein Data Bank.

Other transferrin and lactoferrin receptor-binding agents may be identified using methods known in the art, for example, using biopanning methods (see, e.g., Lee et al. (2004) Eur. J. Biochem. 268:2004-2012) or in silico methods (see, e.g., Tom et al. (2003) Chemistry and Biology 10, 759-767; Kuo et al. (2003) J. Med. Chem. 46, 4021-4031; Nilsson et al. (2003) J. Med. Chem. 46, 3985-4001; Bjerrum et al. (2003) J. Med. Chem. 46, 2246-2249).

The structural and functional characteristics of transferrin and lactoferrin receptors from various vertebrate animal species have been compared to the human receptors (Lim B C, McArdle H J, Morgan E H. J Comp Physiol [B]. 1987; 157 (3):363-71; van Bockxmeer F M, Morgan E H. Comp Biochem Physiol A. 1982; 71(2):211-8). Transferrin and lactoferrin receptor-binding agents that more specifically target non-human vertebrate animal species can be prepared by the methods disclosed herein, and coupled to the endoperoxides, including artemisinin-related endoperoxides, by the methods of the invention.

Another embodiment includes compositions comprising a compound comprising at least one endoperoxide containing moiety covalently linked to a receptor binding agent that binds to a transferrin receptor or a lactoferrin receptor on a cell without interfering with transferrin or lactoferrin binding to the same receptor, and a pharmaceutically acceptable carrier.

Another embodiment of the invention includes a method of treating a disease or condition elected from the group consisting of cancer; restenosis; proliferative eye, kidney, and skin diseases; precancerous hyperplastic conditions, e.g., benign prostatic hyperplasia (BPH) and benign breast disease

TABLE 2

Atomic coordinates of surface cavities of the B-chain of transferrin receptor in 1SUV

| ATOM | 30007 | H7  | SPH | 907 | 29.202 | 15.243 | −28.609 | 1.00 | 36.67 | PATB | 6  |
| ATOM | 30019 | H19 | SPH | 919 | 4.766  | 21.399 | −22.762 | 1.00 | 25.97 | PATB | 18 |
| ATOM | 30033 | H33 | SPH | 933 | 13.192 | 2.473  | −30.135 | 1.00 | 18.15 | PATB | 32 |
| ATOM | 30034 | H34 | SPH | 934 | 21.175 | 27.910 | −11.692 | 1.00 | 17.94 | PATB | 33 |
| ATOM | 30043 | H43 | SPH | 943 | 36.539 | 25.067 | −39.182 | 1.00 | 15.13 | PATB | 42 |
| ATOM | 30050 | H50 | SPH | 950 | 24.774 | 8.593  | −25.987 | 1.00 | 12.18 | PATB | 49 |
| ATOM | 30054 | H54 | SPH | 954 | 32.285 | 22.875 | −0.665  | 1.00 | 10.12 | PATB | 53 |
| ATOM | 30060 | H60 | SPH | 960 | 33.907 | 7.338  | 4.480   | 1.00 | 9.27  | PATB | 59 |
| ATOM | 30062 | H62 | SPH | 962 | 9.972  | 22.189 | −14.193 | 1.00 | 8.96  | PATB | 61 |
| ATOM | 30063 | H63 | SPH | 963 | 16.245 | 8.306  | −38.876 | 1.00 | 8.63  | PATB | 62 |
| ATOM | 30067 | H67 | SPH | 967 | 21.718 | −2.591 | 5.229   | 1.00 | 7.44  | PATB | 66 |
| ATOM | 30076 | H76 | SPH | 976 | 23.955 | 14.153 | −19.834 | 1.00 | 5.89  | PATB | 75 |
| ATOM | 30086 | H86 | SPH | 986 | 28.386 | 30.523 | −9.090  | 1.00 | 2.98  | PATB | 85 |
| ATOM | 30089 | H89 | SPH | 989 | 23.244 | −1.459 | −39.902 | 1.00 | 1.83  | PATB | 88 |
| ATOM | 30091 | H91 | SPH | 991 | 19.128 | −9.924 | −30.585 | 1.00 | 1.70  | PATB | 90 |

These target cavities are of a diameter of 8-15 Å with various shapes and polarities. Visual inspection suggested that all the target cavities are easily accessible from the surface through a wide opening.

In one aspect, the covalent conjugates of the invention comprise a receptor binding agent that binds to a transferrin receptor or a lactoferrin receptor without interfering with transferrin or lactoferrin binding to the receptor. Two peptides with a sequence of HAIYPRH (SEQ ID NO: 1) and THRPP-MWSPVWP (SEQ ID NO: 2) have been shown to bind to the human transferrin receptor without interfering with transferrin binding (Lee et al. (2004) Eur. J. Biochem. 268:2004-2012). In addition, virus-derived peptides have also been identified that can bind to the human transferrin receptor without interfering with transferrin binding (Zhang et al (2003) J. Virol. 77, 10468-10478; Xia et al. (2000) J. Virol. 74, 11359-11366; Palermo et al. (2003) J. Virol. 77, 8915-8923). All these peptides are likely to bind to one or more target cavities.

(BBD); autoimmune disease; arthritis; graft rejection; inflammatory bowel disease; proliferation induced after medical procedures; an infection by a pathogenic organism that has a receptor for an iron-carrying protein selected from the group consisting of transferrin and lactoferrin; topical bacterial infections; gingivitis; skin infections; and eye infections; comprising administering to said subject an effective amount of a composition comprising a compound comprising at least one endoperoxide containing moiety covalently linked to a receptor binding agent that binds to a transferrin receptor or a lactoferrin receptor on a cell without interfering with transferrin or lactoferrin binding to the receptor. One embodiment includes a method where the disease or condition is selected from the group consisting of cancer and precancerous hyperplastic conditions, such as BPH and BBD. The methods include compounds wherein the endoperoxide containing moiety comprises an endoperoxide bridge. In some embodiments, the endoperoxide bridge is a 1,2,4-trioxane bridge or a 1,2,4,5 tetraoxane bridge. In preferred embodiments, the endoperoxide containing moiety is an artemisinin-related endoperoxide.

The covalent conjugates of the invention have high binding affinity for the transferrin receptor and do not interfere with receptor binding of transferrin. The attached endoperoxide is then transported into cancer cells concomitantly with transferrin, which will provide the iron for activation of the endoperoxide inside the cell (FIG. 1). Since these are small synthetic molecules, they may be easily administered in relatively large quantities. In some embodiments, the covalent conjugates of the invention comprise endoperoxide-tagged peptides, as described in Examples 9-12.

As described above, the covalent conjugates of the invention are useful for treating cancer and precancerous hyperplastic conditions. The covalent conjugates of the invention are also useful for treating infections by pathogenic organisms that have receptors for the iron-carrying proteins such as transferrin or lactoferrin. To establish a successful infection, a pathogen must overcome the strict iron limitations imposed by the host. To overcome this limitation, many pathogens obtain iron from iron-carrying host proteins (see, e.g., Cornelissen, (2003) *Front. Biosci.* 8:D836-847). For example, *Neisseria meningitidis*, the causative agent of bacterial meningitis, expresses cell surface receptors for the iron-carrying proteins transferrin and lactoferrin (Evans and Oakhill (2002) *Biochem. Soc. Trans.* 30(4):705-707), *Helicobacter pylori*, the etiologic agent of gastritis and peptic ulcer disease in humans, expresses a receptor for human lactoferrin (Husson et al. (1993) *Infect. Immun.* 61(6):2694-2697), and *Staphylococcus aureus* expresses receptors for hemoglobin (Mazmanian et al. (2003) *Science* 299:906-909) Thus, the covalent conjugates of the invention are useful for killing pathogenic organisms (such as bacterial or fungi) that have receptors that bind the transferrin or lactoferrin receptor-binding agent in the conjugate. For example, a covalent conjugate between an artemisinin-related endoperoxide and a receptor-binding agent that binds to pathogenic organism cell surface receptors that binds host holotransferrin or hololactoferrin may be used to treat bacterial meningitis caused by *N. meningitidis* or gastritis and peptic ulcer disease caused by *Helicobacter pylori*.

To prepare the covalent conjugates of the invention, endoperoxides are covalently linked (or tagged) to transferrin or lactoferrin receptor-binding agents using well-known methods (see, e.g., Chen et al. (2005) *J. Med. Chem.* 48, 1098-1106; Thumshirn et al. (2003) *Chem. Eur. J.* 9:2717-2725). Exemplary methods for preparing covalent conjugates of the invention are provided in Examples 1-12.

The covalent conjugates may be purified by using standard methods in the art, for example by using gel-filtration chromatography, ion-exchange, and reverse-phase or hydrophobic interaction High-Pressure Liquid Chromatography (HPLC). The number of molecules of endoperoxide bound to one molecule of transferrin receptor-binding agent may be determined by using standard methods in the art, for example ion-spray mass spectrometry. The ratio of endoperoxide to transferrin receptor-binding agents in the covalent conjugates will depend on the transferrin receptor-binding agent being used and the method of forming the conjugate.

According to the methods of the invention, the covalent conjugates between an endoperoxide and a transferrin or lactoferrin receptor-binding agent have cytotoxic activities when administered to cancer cells. In addition, the covalent conjugates of the invention are effective at killing pathogens with receptors that bind transferrin or lactoferrin. The invention also provides compositions comprising the covalent conjugates of the invention.

The invention also provides methods for administering compositions comprising a covalent conjugate between an endoperoxide and transferrin or lactoferrin receptor-binding agent to a subject in need thereof. The covalent conjugates between endoperoxides and a transferrin or lactoferrin receptor-binding agent are as described above.

These methods are applicable to any animal subject, such as a human subject. For example, a subject in need of compositions comprising a covalent conjugate of the invention may be a cancer patient. As described above, rapidly proliferating cells such as cancer cells generally possess higher concentrations of cell surface transferrin receptors. The methods provide a mechanism for selectively delivering both the endoperoxide moiety and the iron it reacts with to rapidly proliferating cells, such as cancer cells. Accordingly, the invention provides methods for treating cancer by administering to a human or animal subject in need thereof an effective amount of a compound comprising a covalent conjugate between an endoperoxide and a transferrin or lactoferrin receptor-binding agent. Other conditions in which there is an abnormal hyperproliferation of cells and which may be treated with the covalent conjugates of the invention include, but are not limited to, restenosis, proliferative eye, kidney, and skin diseases, precancerous hyperplastic conditions, e.g., benign pro static hyperplasia (BPH) and benign breast disease (BBD), autoimmune disease, arthritis, graft rejection, inflammatory bowel disease, or proliferation induced after medical procedures.

The compounds and compositions comprising a covalent conjugate between an endoperoxide and a transferrin or lactoferrin receptor-binding agent may also be administered for treating an infection by a pathogen expressing cell-surface receptors for the transferrin or lactoferrin receptor-binding agent in the covalent conjugate. As used herein, the term "treating an infection by a pathogen" refers to inhibiting the growth of the pathogen and/or preventing or ameliorating the symptoms of disease associated with the infection.

Another embodiment of the invention therefore includes compounds wherein the transferrin receptor binding agent is a peptide. Preferred compounds include those wherein the transferring receptor binding agent is a peptide that binds to the human transferrin receptor without interfering with transferrin binding. The peptide, for example, may be selected from the group consisting of SEQ ID NO: 1 and SEQ ID NO: 2.

As described above, the covalent conjugates of the invention are useful for treating cancer and precancerous hyperplastic conditions. The covalent conjugates of the invention are also useful for treating infections by pathogenic organisms that have receptors for the iron-carrying proteins such as transferrin or lactoferrin. To establish a successful infection, a pathogen must overcome the strict iron limitations imposed by the host. To overcome this limitation, many pathogens obtain iron from iron-carrying host proteins (see, e.g., Cornelissen, (2003) *Front. Biosci.* 8:D836-47). For example, *Neisseria meningitidis*, the causative agent of bacterial meningitis, expresses cell surface receptors for the iron-carrying proteins transferrin and lactoferrin (Evans and Oakhill (2002) *Biochem. Soc. Trans.* 30(4):705-7), *Helicobacter pylori*, the etiologic agent of gastritis and peptic ulcer disease in humans, expresses a receptor for human lactoferrin (Husson et al. (1993) *Infect. Immun.* 61(6):2694-7), and *Staphylococcus aureus* expresses receptors for hemoglobin (Mazmanian et al. (2003) *Science* 299:906-9) Thus, the covalent conjugates of the invention are useful for killing pathogenic organisms (such as bacterial or fungi) that have receptors that are bound by the transferrin or lactoferrin receptor-binding agent in the conjugate. For example, a covalent conjugate between an artemisinin-related endoperoxide and a receptor-binding agent that binds to pathogenic organism cell surface receptors that binds host holotransferrin or hololactoferrin may be used to treat bacterial meningitis caused by N. meningitidis or gastritis and peptic ulcer disease caused by Helicobacter pylori.

Thus in one aspect the compounds and compositions comprising a covalent conjugate between an artemisinin-related endoperoxide and a transferrin or lactoferrin receptor-binding agent may also be administered for treating an infection by a pathogen expressing cell-surface receptors for the transferrin or lactoferrin receptor-binding agent in the covalent conjugate. As used herein, the term "treating an infection by a pathogen" refers to inhibiting the growth of the pathogen and/or preventing or ameliorating the symptoms of disease associated with the infection.

Exemplary pathogens with receptors for iron-carrying host proteins are described above and include Neisseria meningitidis, which expresses a receptor for human transferrin and H. pylori, which expresses a receptor for human lactoferrin. S. aureus has recently been shown to express a receptor for hemoglobin (Mazmanian et al. (2003) Science 299:906-9), and similar proteins are also expressed by Listeria monocytogenes and Bacillus anthracis (Cabanes et al. (2002) Trends. Microbiol. 10(5):238-45). An exemplary list of pathogens that express receptors for iron-carrying host proteins are shown in Table 3. Once the iron-carrying protein is bound to the receptor expressed by pathogen, the iron or heme is generally released from the iron-carrying protein and transported into the cell (see, e.g., Gray-Owens and Schryvers (1996) Trends Microbiol. 4(5):185-91; Wandersman and Stojiljkovic (2000) Curr. Op. Microbiol. 3:215-20).

TABLE 3

Receptors for Iron-Carrying Proteins in Human and Animal Pathogens

| Pathogen | Host | Disease | Receptor |
|---|---|---|---|
| Moraxella bovis | Bovine | Kerato-conjunctivitis | Transferrin, lactoferrin[1] |
| Moraxella catarrhalis | Human | Otitis media | Transferrin, lactoferrin[1] |
| Moraxella lacunata | Human | Kerato-conjunctivitis | Transferrin, lactoferrin[1] |
| Neisseria meningitidis | Human | Meningitis | Transferrin, lactoferrin, hemoglobin[1,19] |
| Neisseria gonorrheae | Human | Gonorrhea | Transferrin, lactoferrin, hemoglobin[1,18] |
| Actinobacillus actinomycetecomitans | Human | Juvenile periodontitis | Transferrin[1] |
| Actinobacillus equuli | Equine | Septicemia | Transferrin[1] |
| Actinobacillus pleuropneumoniae | Porcine | Pneumonia | Transferrin[1] |
| Haemophilus agnii | Ovine | Septicemia | Transferrin[1] |
| Haemophilus avium | Poultry | Sinusitis | Transferrin[1] |
| Haemophilus influenzae | Human | Meningitis, otitis media | Transferrin, hemoglobin[1,20] |
| Haemophilus paragallinarum | Poultry | Infectious coryza | Transferrin[1] |
| Haemophilus somnus | Bovine | Thromboembolic meningoencephalitis | Transferrin[1] |
| Haemophilus parasuis | Porcine | Glasser's disease | Transferrin[1] |
| Haemophilus ducreyi | Human | Genital ulcer disease | Hemoglobin[15] |
| Pasteurella haemolytica | Bovine, ovine, caprine | Shipping fever, pasteurellosis | Transferrin[1] |
| Pasteurella multocida | Bovine | Pneumonia, septicemia | Transferrin[1] |
| Staphylococcus aureus | Human | Bacteremia, pneumonia, endocarditis, septic arthritis, osteomyelitis, deep abscesses, food poisoning | Transferrin, hemoglobin[2,13] |
| Staphylococcus epidermidis | Human | Endocarditis, endopthalmitis, septicemia, cystitis | Transferrin[2] |
| Streptococcus pneumoniae | Human | Pneumonia, meningitis, bacteremia, otitis media | Lactoferrin[3] |
| Leishmania chagasi | Human | Leishmaniasis | Transferrin, lactoferrin[4] |
| Escherichia coli K88 | Porcine | Enteropathogenesis | Transferrin[5] |
| Tritrichonomas foetus | Cattle | Trichomoniasis | Lactoferrin, hemoglobin[6,] |
| Treponema pallidum | Human | Syphilis | Lactoferrin[7] |
| Mycoplasma pneumonia | Human | Pneumonia | Lactoferrin[8] |
| Bordetella pertussis | Human | Whooping cough | Lactoferrin[9] |
| Trichonomas vaginalis | Human | Vaginosis | Lactoferrin[10] |
| Aeromonas salmonicida | Fish | Furunculosis | Transferrin, lactoferrin[11] |
| Helicobacter pylori | Human | Gastritis, gastric and duodenal ulcers, gastric adenocarcinoma, lymphoma | Lactoferrin[12] |
| Yersinia enterocolitica | Human | Enteritis | Hemoglobin, myoglobin, hemopexin, catalase, albumin-heme[14] |
| Vibrio vulnificus | Eel | Food poisoning, septicemia, wound infections | Hemoglobin[16] |

TABLE 3-continued

Receptors for Iron-Carrying Proteins in Human and Animal Pathogens

| Pathogen | Host | Disease | Receptor |
|---|---|---|---|
| Porphyromonas gingivalis | Human | Periodontal disease | Hemoglobin[17] |

[1] Gray-Owen and Schryvers (1996) Trends Microbiol. 4(5): 185-191
[2] Modun et al. (1998) Infect. Immun. 66(8): 3591-3596
[3] Hammerschmidt et al. (1999) Infect. Immun. 67(4): 1683-1687
[4] Britigan et al. (1998) Adv. Exp. Med. Biol. 443: 135-140
[5] Grange et al. (1997) Adv. Exp. Med. Biol. 412: 357-361
[6] Tachezy et al. (1996) Exp. Parasitol. 83(2): 216-228
[7] Alderete et al. (1988) Genitourin. Med. 64(6): 359-363
[8] Tryon and Baseman (1987) Microb. Pathog. 3(6): 437-443
[9] Redhead et al. (1987) J. Gen. Microbiol. 133(4): 891-898
[10] Peterson and Alderete (1984) J. Exp. Med. 160(2): 398-410
[11] Chart and Trust (1983) J. Bacteriol. 156(2): 758-764
[12] Dhaenens et al. (1997) Infect. Immun. 65(2): 514-518
[13] Mazmanian et al. (2003) Science 299: 906-909
[14] Bracken et al. (1999) J. Bacteriol. 181(19): 6063-6072
[15] Al-Twafiq et al. (2000) J. Infect. Dis. 181(3): 1049-1054
[16] Fouz et al. (1997) Microbiol. Lett. 156(2): 187-191
[17] Simpson et al. (2000) J. Bacteriol. 182(10): 5737-5748
[18] Chen et al. (1996) Infect. Immun. 64: 5008-5014
[19] Stojiljkovic et al. (1996) J. Bacteriol. 179(15): 4670-4678
[20] Frangipane et al. (1994) FEMS Microbiol. Lett. 118: 243-248

This invention may also be useful for the treatment of infection by bacterial pathogens that invade host cells, e.g., *Mycobacterium tuberculosis*. The invasion induces an increased expression of transferrin/lactoferrin receptors on the surface of host cells, thus, leading to an increased uptake of iron (Olakanmi et al. (2004) *Infect. Immun.* 72:2022-2028). The covalent conjugate could kill the host cell and bacteria within by the mechanism described above.

In one aspect, the methods of this aspect of the invention provide a mechanism for selectively delivering an endoperoxide moiety and the iron it reacts with directly to the cell membrane of a pathogenic organisms or a cell infected by a pathogenic organism by binding of the covalent conjugate to a receptor for iron-carrying protein. According to the methods of the invention, the endoperoxide moiety in the bound covalent conjugate reacts with the iron, producing harmful free radicals in close proximity to the pathogen.

Other exemplary infections that may be treated by administering an effective amount of a composition comprising a covalent conjugate of the invention include topical bacterial infections, such as gingivitis, skin, and eye infections.

Effective amounts of the covalent conjugates will generally range up to the maximally tolerated dosage, but the concentrations are not critical and may vary widely. The precise amounts employed by the attending physician will vary, of course, depending on the compound, route of administration, physical condition of the patient and other factors. The daily dosage may be administered as a single dosage or may be divided into multiple doses for administration.

The amount of the conjugates of the invention actually administered will be a therapeutically effective amount, which term is used herein to denote the amount needed to produce a substantial beneficial effect. Effective doses may be extrapolated from dose-response curves derived from in vitro or animal model test systems. The animal model is also typically used to determine a desirable dosage range and route of administration. Such information can then be used to determine useful doses and routes for administration in humans or other mammals. The determination of an effective dose is well within the capability of those skilled in the art. Thus, the amount actually administered will be dependent upon the individual to which treatment is to be applied, and will preferably be an optimized amount such that the desired effect is achieved without significant side-effects.

Therapeutic efficacy and possible toxicity of the covalent conjugates of the invention may be determined by standard pharmaceutical procedures, in cell cultures or experimental animals (e.g., $ED_{50}$, the dose therapeutically effective in 50% of the population; and $LD_{50}$, the dose lethal to 50% of the population). The dose ratio between therapeutic and toxic effects is the therapeutic index, and it can be expressed as the ratio $LD_{50}$ to $ED_{50}$. Covalent conjugates that exhibit large therapeutic indices are particularly suitable in the practice of the methods of the invention. The data obtained from cell culture assays and animal studies may be used in formulating a range of dosage for use in humans or other mammals. The dosage of such conjugates lies preferably within a range of circulating concentrations that include the $ED_{50}$ with little or no toxicity. The dosage typically varies within this range depending upon the dosage form employed, sensitivity of the patient, and the route of administration. Thus, optimal amounts will vary with the method of administration, and will generally be in accordance with the amounts of conventional medicaments administered in the same or a similar form.

The covalent conjugates of the invention may be administered alone, or in combination with one or more additional therapeutically active agents. For example, in the treatment of cancer, the conjugates may be administered in combination with therapeutic agents including, but not limited to, androgen inhibitors, such as flutamide and luprolide; antiestrogens, such as tomoxifen; antimetabolites and cytotoxic agents, such as daunorubicin, fluorouracil, floxuridine, interferon alpha, methotrexate, plicamycin, mercaptopurine, thioguanine, adriamycin, carmustine, lomustine, cytarabine, cyclophosphamide, doxorubicin, estramustine, altretamine, hydroxyurea, ifosfamide, procarbazine, mutamycin, busulfan, mitoxantrone, carboplatin, cisplatin, streptozocin, bleomycin, dactinomycin, and idamycin; hormones, such as medroxyprogesterone, estramustine, ethinyl estradiol, estradiol, leuprolide, megestrol, octreotide, diethylstilbestrol, chlorotrianisene, etoposide, podophyllotoxin, and goserelin; nitrogen mustard derivatives, such as melphalan, chlorambucil, methlorethamine, and thiotepa, steroids, such as betamethasone; and other antineoplastic agents, such as live *Mycobacterium bovis*, dicarbazine, asparaginase, leucovorin, mitotane, vincristine, vinblastine, and taxotere. Appropriate amounts in each case will vary with the particular agent, and will be either readily known to those skilled in the art or readily determinable by routine experimentation.

The covalent conjugates of the invention may also be administered in combination with an agent that increases iron transport into cells, for example, by increasing the cell surface number of receptors for the iron-carrying protein in the conjugate. It has been shown for example, that insulin, insulin-like growth factor I, and epidermal growth factor cause an increase in the number of transferrin receptors at the cells surface (see, e.g., Davis et al. (1987) *J. Biol. Chem.* 261(19): 8708-11; Davis et al. (1986) *J. Biol. Chem.* 262(17):13126-34). Therefore, in some embodiments, covalent conjugates of the invention are administered in combination with insulin, insulin-like growth factor I, or epidermal growth factor.

The covalent conjugates of the invention may also be combined with agents such as cytokines, growth factors, and other compounds that are iron-regulating molecules that enhance TfR expression and/or intracellular iron to facilitate the treatment of cancer, hyperproliferative disorders, inflammation, and infectious diseases. Table 4 illustrates a non-limiting set of exemplary compounds that may be used in combination with the covalent conjugates of the invention.

The covalent conjugates of the invention may be formulated into a composition that additionally comprises suitable pharmaceutically acceptable carriers, including excipients and other compounds that facilitate administration of the covalent conjugate to a mammalian subject. Further details on techniques for formulation and administration may be found in the latest edition of "Remington's Pharmaceutical Sciences" (Mack Publishing Co, Easton, Pa.).

Compositions for oral administration may be formulated using pharmaceutically acceptable carriers well known in the art, in dosages suitable for oral administration. Such carriers enable the compositions containing covalent conjugates of the invention to be formulated as tablets, pills, dragees, capsules, liquids, gels, syrups, slurries, suspensions, etc., suitable for ingestion by a subject. Compositions for oral use may be formulated, for example, in combination with a solid excipient, optionally grinding the resulting mixture, and processing the mixture of granules, after adding suitable additional compounds, if desired, to obtain tablets or dragee cores. Suitable excipients include carbohydrate or protein fillers. These include, but are not limited to, sugars, including lactose, sucrose, mannitol, or sorbitol, starch from corn, wheat, rice,

TABLE 4

Combination Therapies

| Molecule | Effect on Iron Metabolism | Clinical Target |
|---|---|---|
| Erythropoietin (Weiss G, et al. Blood. 1997 Jan. 15; 89(2): 680-7; Vreugdenhil G, et al. Ann Hematol. 1992 December; 65(6): 265-8.) | Enhance binding affinity of iron-regulatory protein (IRP)-1 Increase in transferrin receptor mRNA levels in K562 and MEL Enhance cell surface expression of TfR Increase uptake of iron into cells. | Cancer (Leukemia) |
| Interleukin-4 (Weiss G, et al. J Immunol. 1997 Jan. 1; 158(1): 420-5.) | Enhance iron uptake and storage in activated macrophages Increase ferritin translation IRP-independent augmentation of TfR mRNA expression. | Infectious and Inflammatory Diseases |
| Interleukin-10 (Ludwiczek S, et al. Blood. 2003 May 15; 101(10): 4148-54. Epub 2003 Jan. 9) | Stimulates TfR-mediated iron uptake into activated monocytes | Infectious and Inflammatory Diseases |
| Interleukin-13 (Weiss G, et al. J Immunol. 1997 Jan. 1; 158(1): 420-5.) | Enhance iron uptake and storage in activated macrophages Increase ferritin translation IRP-independent augmentation of TfR mRNA expression. | Infectious and Inflammatory Diseases |
| Dexrazoxane (Weiss G, et al. Biochem Pharmacol. 1997 May 15; 53(10): 1419-24) | Enhance the binding affinity of iron regulatory protein (IRP) Increase TfR surface expression Enhance cellular iron uptake Enhance cellular sequestration of iron | Cancer (Leukemia) |

Administration of the covalent conjugates of the invention is accomplished by any effective route, e.g., parenterally or orally. Methods of administration include topical (for examples, skin patches), inhalational, buccal, intraarterial, subcutaneous, intramedullary, intravenous, intranasal, intrarectal, intraocular administration, and other conventional means. For example, the covalent conjugates may be injected directly into a tumor, into the vicinity of a tumor, or into a blood vessel that supplies blood to the tumor.

potato, or other plants; cellulose such as methyl cellulose, hydroxypropylmethyl-cellulose, or sodium carboxymethyl-cellulose; and gums including arabic and tragacanth; as well as proteins, such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage).

Covalent conjugates for oral administration may be formulated, for example, as push-fit capsules made of gelatin, as well as soft, sealed capsules made of gelatin and a coating such as glycerol or sorbitol. Push-fit capsules may contain covalent conjugates mixed with filler or binders such as lactose or starches, lubricants such as talc or magnesium stearate, and, optionally, stabilizers. In soft capsules, the covalent conjugates may be dissolved or suspended in suitable liquids, such as fatty oils, liquid paraffin, or liquid polyethylene glycol with or without stabilizers.

Compositions for parenteral administration include aqueous solutions of one or more covalent conjugates of the invention. For injection, the covalent conjugates may be formulated in aqueous solutions, such as in physiologically compatible buffers such as Hank's solution, Ringer's solution, or physiologically buffered saline. Aqueous injection suspensions may contain substances, which increase the viscosity of the suspension, such as sodium carboxymethyl cellulose, sorbitol, or dextran. Additionally, suspensions of the covalent conjugates may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents, which increase the solubility of the covalent conjugate to allow for the preparation of highly concentrated solutions.

For topical or nasal administration, penetrants appropriate to the particular barrier to be permeated are typically used in the formulation. Examples of these are 2-pyrrolidone, N-methyl-2-pyrrolidone, dimethylacetamide, dimethyl-formamide, propylene glycol, methyl or isopropyl alcohol, dimethyl sulfoxide, and azone. Additional agents may further be included to make the formulation cosmetically acceptable. Examples of these are fats, waxes, oils, dyes, fragrances, preservatives, stabilizers, and surface-active agents. Keratolytic agents such as those known in the art may also be included. Examples are salicylic acid and sulfur. For topical administration, the composition may be in the form of a transdermal ointment or patch for systemic delivery of the compound and may be prepared in a conventional manner (see, e.g., Barry, Dermatological Formulations (Drugs and the Pharmaceutical Sciences-Dekker); Harrys Cosmeticology (Leonard Hill Books).

For rectal administration, the compositions may be administered in the form of suppositories or retention enemas. Such compositions may be prepared by mixing the covalent conjugates with a suitable non-irritating excipient that is solid at ordinary temperatures but liquid at the rectal temperature and will therefore melt in the rectum to release the drug. Suitable excipients include, but are not limited to, cocoa butter and polyethylene glycols.

The amounts of each of these various types of additives will be readily apparent to those skilled in the art, optimal amounts being the same as in other, known formulations designed for the same type of administration. Stratum corneum penetration enhancers, for example, will typically be included at levels within the range of about 0.1% to about 15%.

Compositions containing the covalent conjugates of the present invention may be manufactured in a manner similar to that known in the art (e.g., by means of conventional mixing, dissolving, granulating, dragee-making, levigating, emulsifying, encapsulating, entrapping or lyophilizing processes). The compositions may also be modified to provide appropriate release characteristics, e.g., sustained release or targeted release, by conventional means (e.g., coating).

Compositions containing the covalent conjugates may be provided as a salt and can be formed with many acids, including but not limited to hydrochloric, sulfuric, acetic, lactic, tartaric, malic, succinic, etc. Salts tend to be more soluble in aqueous or other protonic solvents than are the corresponding free base forms.

After compositions formulated to contain covalent conjugates and an acceptable carrier have been prepared, they can be placed in an appropriate container and labeled for use.

EXAMPLES

The foregoing discussion may be better understood in connection with the following representative examples, which are presented for purposes of illustrating the principle methods and compositions of the invention and not by way of limitation. Various other examples will be apparent to the person skilled in the art after reading the present disclosure without departing from the spirit and scope of the invention. It is intended that all such other examples be included within the scope of the appended claims.

Figure 2:
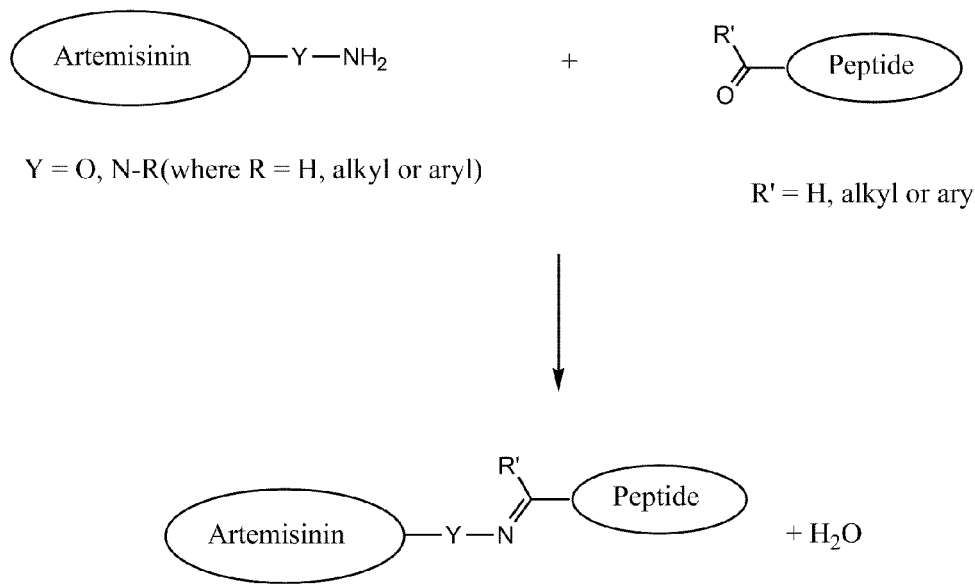
FIG. 2 shows a schematic diagram of the synthesis of artemisinin-peptide conjugates, which are generally prepared by reacting a carbonyl-containing peptide with artemisinin derivatives that carry a hydrazine (R,R'—N—NH$_2$) or aminoxy (R—O—NH$_2$) group.

The covalent conjugates of the invention are generally prepared by reacting a carbonyl-containing peptide with an endoperoxide moiety that carries a hydrazine (R,R'—N—NH$_2$) or aminoxy (R—O—NH$_2$) group (FIG. 2). The linker between the endoperoxide moiety and the receptor binding agent, such as a peptide, can be by any covalent bond means, including but not limited to hydrazones, oxime, amides, esters, ethers, and thioethers. All the linear peptides have at least one amino group at the N-terminus end, and artemisinin or other endoperoxides can be attached to the peptide by using the chemistry described here. In the sections below, the synthesis of these compounds and their reaction to produce artemisinin-tagged peptides is described.

All parts are by weight, and temperatures are indicated in degrees centigrade (° C.), unless otherwise indicated.

Example 1

Synthesis of 4-formylbenzoyl-His-Ala-Ile-Tyr-Pro-Arg-His-amide (HAIYPRH)

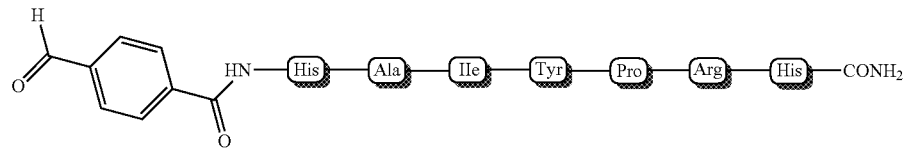

Fmoc-Rink amide resin (0.5 g) was placed in a 10 mL reaction vessel. Fmoc-Ala, Fmoc-Ile, Fmoc-Tyr(tBu), Fmoc-His(Trt) and Fmoc-Arg(PMC) were sequentially coupled to assemble the desired peptide on the resin. After the final Fmoc group was deprotected with 20% piperidine in DMF, 4-Formylbenzoic acid was coupled to introduce a carbonyl group at the N-terminus of the peptide. The peptide was cleaved from the resin in 5 mL of 20% TFA (trifluoroacetic acid) in $CH_2Cl_2$ for 15 min. The resin was removed by filtration, and washed with $CH_2Cl_2$ three times. The filtrate and washings were combined, and concentrated to approximately 2 mL. Dry ether (30 mL) was added the residue to precipitate the peptide. The precipitates were collected by centrifugation and washed three times with ether. After vacuum drying, the crude product (0.3 gram) was obtained and the peptide was purified by reverse phase HPLC. The C4 reverse-phase column was used with a linear gradient from 100% water (0.1% TFA) to 60% acetonitrile-40% water (0.1% TFA). The peptide was detected by the absorbance at 270 nm. The yield was 0.1 gram. Ion-spray MS: m/z=1024.2 (M+H)±.

Example 2

Synthesis of 6-oxo-heptanoyl-His-Ala-Ile-Tyr-Pro-Arg-His-amide (HAIYPRH)

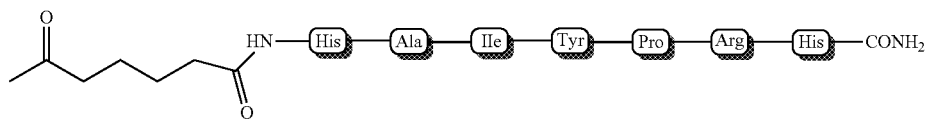

Fmoc-Rink amide resin (0.5 g) was placed in a 10 mL reaction vessel. Fmoc-Ala, Fmoc-Ile, Fmoc-Tyr(tBu), Fmoc-His(Trt) and Fmoc-Arg(PMC) were sequentially coupled to assemble the desired peptide on the resin. After the final Fmoc group was deprotected with 20% piperidine in DMF, 6-oxo-heptanoic acid was coupled to introduce a carbonyl group at the N-terminus of the peptide. The peptide was cleaved from the resin in 5 mL of 20% TFA (trifluoroacetic acid) in $CH_2Cl_2$ for 15 min. The resin is removed by filtration, and washed with $CH_2Cl_2$ three times. The filtrate and washings were combined, and concentrated to approximately 2 mL. Dry ether (30 mL) was added to the residue to precipitate the peptide. The precipitates were collected by centrifugation, and three times washed with ether. After vacuum drying, the crude product (0.3 gram) was obtained, and the peptide purified by reverse phase HPLC. The C4 reverse-phase column was used with a linear gradient from 100% water (0.1% TFA) to 60% acetonitrile-40% water (0.1% TFA). The peptide was detected by the absorbance at 270 nm. The yield was 0.1 gram. Ion-spray MS: m/z=1018.4 $(M+H)^+$ and 1040.4 $(M+Na)^+$.

Example 3

Synthesis of bis(4-formylbenzoyl)Lys-His-Ala-Ile-Tyr-Pro-Arg-His-amide (HAIYPRH)

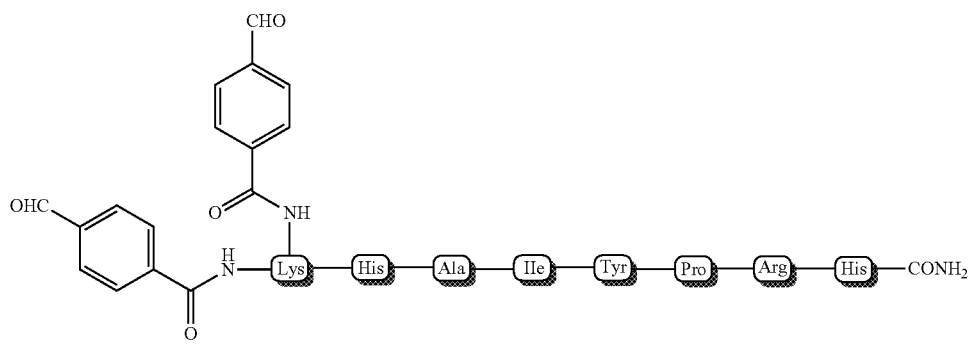

Fmoc-Rink amide resin (0.5 g) was placed in a 10 mL reaction vessel. Fmoc-Ala, Fmoc-Ile, Fmoc-Tyr(tBu), Fmoc-His(Trt), Fmoc-Arg(PMC) and Fmoc-Lys(Boc)$_2$ were sequentially coupled to assemble the desired peptide on the resin. After the final Fmoc group was deprotected with 20% piperidine in DMF, 4-Formylbenzoic acid (2 equivalent) was coupled to the N-terminal Lys residue. The peptide was cleaved from resin in 5 mL of 20% TFA (trifluoroacetic acid) in CH$_2$Cl$_2$ for 15 min. The resin was removed by filtration, and washed with CH$_2$Cl$_2$ three times. The filtrate and washings were combined and concentrated to approximately 2 mL. Dry ether (30 mL) was added to the residue to precipitate the peptide. The precipitates were collected by centrifugation, and washed three times with ether. After vacuum drying, the crude product (0.3 gram) was obtained and the peptide purified by reverse phase HPLC. The C4 reverse-phase column was used with a linear gradient from 100% water (0.1% TFA) to 60% acetonitrile-40% water (0.1% TFA). The peptide was detected by the absorbance at 270 nm. The yield was 0.1 gram. Ion-spray MS: m/z=1284.8 (M+H)$^+$ and 1306.9 (M+Na)$^+$.

Example 4

Synthesis of 5-(Dihydroxyartemisinin-methyl)-2-pyridine carbohydrazide (DHA-Pyr-NH$_2$)

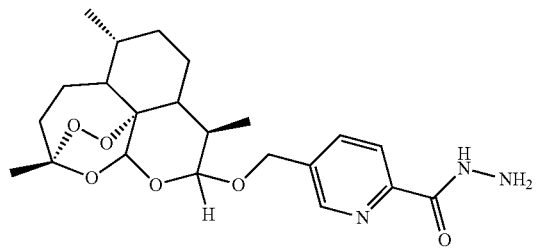 [SMILES: C[C@H]1C(OCc2ccc(C(=O)NN)nc2)OC2O[C@]3(C)CCC4[C@H](C)CCC1[C@@]24OO3]

5-(Dihydroxyartemisinin-methyl)-2-pyridine carbohydrazide (DHA-Pyr-NH$_2$) was synthesized sequentially from Dimethyl-2,5-pyridinedicarboxylate, Pyridine 2,5-dicarboxylic acid 5-methyl ester, 5-Hydroxymethyl-2 ethyl pyridinecarboxylate (EHMP), 5-(Dihydroxyartemisinin-methyl)-2 ethyl pyridinecarboxylate (DHA-Pyr-Ester) as shown below.

Dimethyl-2,5-pyridinedicarboxylate

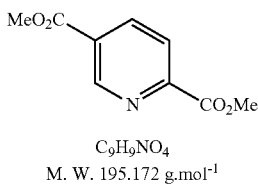 [SMILES: COC(=O)c1ccc(C(=O)OC)nc1]

C$_9$H$_9$NO$_4$
M. W. 195.172 g.mol$^{-1}$

Dimethyl-2,5-pyridinedicarboxylate (inspired from Isagawa, K.; Kawai, M.; Fushizaki, Y. Nippon Kagaku Zasshi, 1967, 88, (5), 553-6; Dawson, M. I.; Cha, R.; Hobbs, P. D.; Chao, W-r; Schiff, L. J. Med. Chem., 1983, 26, 1282-1293; and Hull, K. G.; Visnick, M.; Sheffrom, A. Tetrahedron 1997, 53, 12405-12414) was prepared as described below.

2,5-pyridinedicarboxylic acid (30 g, 0.182 moles) and methanol (300 mL) were mixed together in a 1 L round bottom flask connected to a funnel containing sulfuric acid conc. (16 mL, 0.285 moles). The acid was added dropwise over a period of 30 min, and then the funnel was removed and replaced with a condenser. The mixture was heated at reflux for 16 h, which becomes a brown, and later a yellow, solution. After the reaction cooled to r.t., the slurry was poured in 500 mL of ice water. Sodium bicarbonate solid (30 g) was added to neutralize the pH. The reaction mixture was concentrated with evaporation in a vacuum. The slurry was dissolved with water/chloroform and the compound processed by extraction. The organic layer was dried with brine and then MgSO$_4$ before solvents were evaporated under reduced pressure to yield a pale yellow solid (29.05 g, 83%). NMR $^1$H 300 MHz, CDCl$_3$ (δ, ppm): 9.29 (dd, J=1.5 Hz and 0.6 Hz, 1H, CH), 8.42 (dd, J=6 Hz and 2.1 Hz, 1H, CH), 8.19 (dd, J=7.2 Hz and 0.9 Hz, 1H, CH), 4.02 (s, 3H, CH$_3$), 3.97 (s, 3H, CH$_3$).

Pyridine 2,5-dicarboxylic acid 5-methyl ester

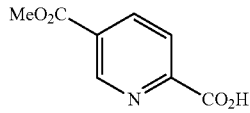

C$_8$H$_7$NO$_4$
M. W. 181.145 g.mol$^{-1}$

Pyridine 2,5-dicarboxylic acid 5-methyl ester (Faul, M. M.; Ratz, A. M.; Sullivan, K. A.; Trankle, W. G.; Winneroski, L. L. J. Org. Chem., 2001, 66, 5772-5782) was produced as described below.

Di-ester (28 g, 0.146 moles) and methanol (260 mL) were stirred in a 500 mL 3-neck round bottom flask with connected a condenser and a funnel. The reaction mixture was heated at reflux after adding one portion of NaOH (6.2 g, 0.155 moles) for 3 h 30 min to produce a white mixture. While at reflux, 2M HCl (121 mL) was added dropwise over a 1 h period to produce a yellow solution. The flask was placed in an ice water bath to cool, and at r.t., a precipitate appears. The precipitate was collected by filtration and washed with 2:1 MeOH/H$_2$O (35 mL) and then water (50 mL). The precipitate was dried overnight. The final yield was 19.68 g (75%). NMR $^1$H 300 MHz, DMSO-d6 (δ, ppm): 9.12 (m, 1H), 8.40 (dd, J=2.1 Hz and 8.1 Hz, 1H, CH), 8.12 (dd, J=0.9 Hz and 8.4 Hz, 1H, CH), 3.89 (s, 3H, CH$_3$). NMR $^{13}$C 75.45 MHz, DMSO-d6 (δ, ppm): 165.9, 165.0, 152.1, 150.2, 138.8, 128.3, 125.0, 53.2.

5-Hydroxymethyl-2 ethyl pyridinecarboxylate (EHMP)

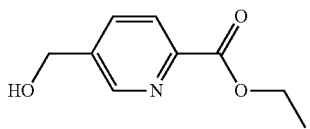

C$_9$H$_{11}$NO$_3$
M. W.: 181.189 g.mol$^{-1}$

The monoester was converted to the corresponding Ca-salt, and then reduced with sodium borohydride to give 5-Hydroxymethyl-2 ethyl pyridinecarboxylate (EHMP). NMR $^1$H 300 MHz, CDCl$_3$ (δ, ppm): 8.63 (b, 1H), 8.05 (broad d, J=7.86 Hz, 1H, CH), 7.83 (dd, J=2.0 Hz and 8.0 Hz, 1H, CH), 4.79 (s, 2H, CH$_2$), 4.42 (q, J=7.1 Hz, CH$_2$), 1.40 (t, J=7.1 Hz, 3H, CH$_3$). NMR $^{13}$C 75.45 MHz, CDCl$_3$ (δ, ppm): 165.0, 148.1, 146.6, 140.8, 135.4, 124.9, 61.9, 61.8, 14.3.

5-(Dihydroxyartemisinin-methyl)-2 ethyl pyridinecarboxylate (DHA-Pyr-Ester)

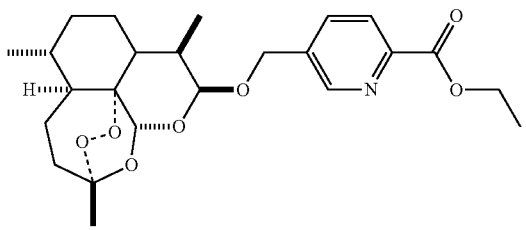

C$_{24}$H$_{33}$NO$_{7}$
M. W.: 447.521 g.mol$^{-1}$

EHMP was then coupled to dihydroartemisinin by the same procedure as described in Example 6 to give 5-(Dihydroxyartemisinin-methyl)-2 ethyl pyridinecarboxylate (ART-Py-ester). The reaction time was 48 h and the yield was 39%. NMR $^1$H 300 MHz, CDCl$_3$ (δ, ppm): 8.69 (b, 1H), 8.07 (broad d, J=7.9 Hz, 1H, CH), 7.71 (dd, J=2.2 Hz and 8.1 Hz, 1H, CH), 5.39 (s, 1H, CH), 4.97 (d, J=13.4 Hz, 1H, CH$_2$), 4.88 (d, J=3.3 Hz, 1H, CH), 4.57 (d, J=13.4 Hz, 1H, CH$_2$), 4.43 (q, J=7.2 Hz, CH$_2$), 2.71-2.61 (m, 1H, CH), 2.38-2.28 (m, 1H, CH), 2.04-1.16 (several m, 16H), 0.93-0.84 (m, 7H). NMR $^{13}$C 75.45 MHz, CDCl$_3$ (δ, ppm): 165.1, 148.6, 147.4, 137.5, 135.4, 124.7, 104.2, 101.9, 88.0, 80.9; 67.1, 61.9, 52.4, 44.2, 37.4, 36.3, 34.5, 30.8, 26.1, 24.6, 24.5, 20.2, 14.3, 13.0.

5-(Dihydroxyartemisinin-methyl)-2-pyridine carbohydrazide (DHA-Pyr-NH$_2$)

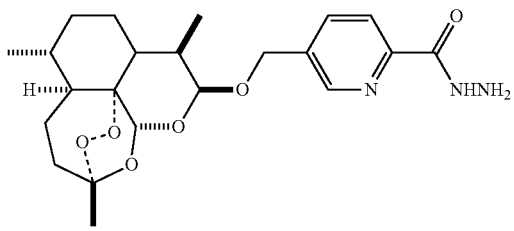

C$_{22}$H$_{31}$N$_{3}$O$_{6}$
M. W.: 433.498 g.mol$^{-1}$

ART-Py-ester was then reacted with hydrazine to obtain the title compound 5-(Dihydroxyartemisinin-methyl)-2-pyridine carbohydrazide. Yield was 83%.

ESI-MS positive (MeOH): 472.4 [M+K]$^+$, 456.4 [M+Na]$^+$, 434.4 [M+H]$^+$, 418.6 [M+H—NH$_2$]$^+$ (100%).

Example 5

Synthesis of 5-(Dihydroxyartemisinin-methyl)-furan-2-carbohydrazide (DHA-Furan-NH$_2$)

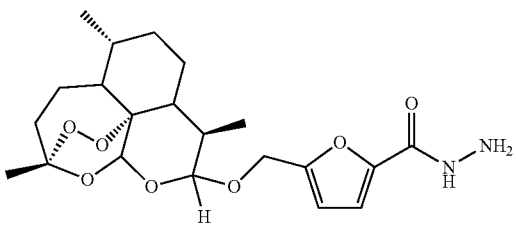 [SMILES: C[C@H]1C(OCc2ccc(C(=O)NN)o2)OC2O[C@]3(C)CCC4[C@H](C)CCC1[C@@]24OO3]

5-(Dihydroxyartemisinin-methyl)-furan-2-carbohydrazide (DHA-Furan-NH$_2$) was synthesized from methyl 5-(hydroxymethyl)-furan-2-carboxylate, methyl 5-(dihydroxyartemisinin-methyl)-furan-2-carboxylate (DHA-Furan-Ester) as shown below.

Methyl 5-(hydroxymethyl)-furan-2-carboxylate

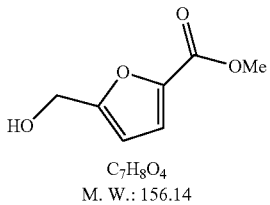 [SMILES: COC(=O)c1ccc(CO)o1]

C$_{7}$H$_{8}$O$_{4}$
M. W.: 156.14

Methyl 5-(hydroxymethyl)-furan-2-carboxylate (Raimundo, B. C.; Oslob, J. D.; Braisted, A. C.; Hyde, J.; McDowell, R. S.; Randal, M.; Waal, N. D.; Wilkinson, J.; Yu, C. H.; Arkin, M. R. *J. Med. Chem.*, 2004, 47 (12), 3111-3130) was synthesized as described below.

5-formyl-2-furan carboxylic acid (1 g, 7.14 mmoles) was stirred in benzene (18 mL)/methanol (4 mL) in a 3-neck 50 mL round bottom flask with one neck connected to a funnel that was previously flushed with nitrogen gas. Trimethylsilyl diazomethane 2M in hexanes (3.6 mL, 7.2 mmoles) was added dropwise over a period of 15 min. After addition, the medium was a green limpid solution, which was stirred for 2 h at r.t. The reaction advancement is monitored by TLC 8:2 Hexanes/AcOEt followed by 95:5 CHCl$_3$/MeOH, and stained with KMnO$_4$. Solvents were evaporated under vacuum, and 14 mL of methanol was added. The flask was placed in an ice-water bath and sodium borohydride (600 mg, 15.8 mmoles) was added. The reaction mixture was stirred for 3 h at r.t. Water was poured off and the mixture extracted with AcOEt. The organic phase was dried over MgSO$_4$, and the solvent was evaporated. The product was purified by silica gel column chromatography (7×3.5 cm) with 100 mL of 90:10, then 200 mL of 80:20, and finally 400 mL of a 75:25 mixture of Hexane/AcOEt to yield a yellow powder after extraction (780 mg, 70%). NMR $^1$H 300 MHz, CDCl$_3$, (δ, ppm): 7.13 (d, J=3.4 Hz, 1H), 6.41 (d, J=3.3 Hz, 1H), 4.67 (d, J=6.2 Hz, 2H), 3.89 (s, 3H).

Methyl 5-(dihydroxyartemisinin-methyl)-furan-2-carboxylate (DHA-Furan-Ester)

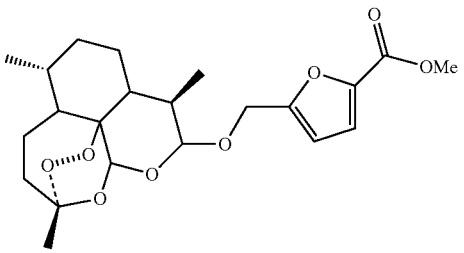

C$_{22}$H$_{30}$O$_{8}$
M. W.: 422.47

Methyl 5-(dihydroxyartemisinin-methyl)-furan-2-carboxylate was synthesized as follows:

DHA was introduced into a 100 mL 3-neck round bottom flask with one neck connected to nitrogen gas, that was previously heated under vacuum and flushed with N$_2$. The flask was flushed with cyclic vacuum/Nitrogen gas (1.261 g, 4.44 mmoles), before benzene (50 mL) the linker (833 mg, 5.34 mmoles in 5 mL benzene) were added. Using a funnel, TMSCl 1M in THF was added dropwise (2.24 mL, 2.24 mmoles). The solution became clear and was covered with aluminum foil for 3 h at r.t. The reaction was monitored by TLC using 8:2 Hexanes/AcOEt, and stained using $I_2$. Hydrolysis, with saturated NaOAc (DI water, 5 mL), changed the color of the solution from green to yellow/orange. The aqueous phase was extracted twice with AcOEt, and the organic phase was washed with 15 mL of NaCl sat, dried over $MgSO_4$, and the solvents evaporated. Hexane was added to the crude mixture. A white precipitate if it appears, is the unreacted DHA. The liquid phase was reddish. Purification was performed by silica gel column chromatography (7×3.5 cm), and using a 9:1 and then 8:2 mixture of Hexanes/AcOEt to elute the product. To separate the alpha product from the beta product, a second silica gel column chromatography was used (25×2.5 cm). Samples (10 mL fractions) were collected during elution with Hexanes/AcOEt: 250 mL 9:1 and then an 8:2 mixture of column solvents. The resulting powder was slightly yellow, which was washed with $Et_2O$ to give a white powder. A 1 h reaction lead to 33% mixture of beta product, 27% DHA, and 8% alpha product. A 3 h reaction was necessary to produce 70% beta linker product. $^1$H-NMR ($CDCl_3$) δ 0.86 (d, J=7.0 Hz), 0.94 (brs, 4H), 1.24 (m, 2H), 1.43 (brs, 4H), 1.60 (m, 3H), 1.87 (m, 1H), 2.02 (m, 1H), 2.37 (m, 1H), 2.64 (brs, 1H), 3.88 (s, 3H), 4.57 (d, J=12.9 Hz), 1H), 4.77 (d, J=13.4 Hz, 1H), 4.89 (brs, 1H), 5.45 (s, 1H), 6.40 (brs, 1H), 7.13 (brs, 1H); $^{13}$C-NMR ($CDCl_3$) δ 13.23, 20.72, 24.84, 25.06, 26.52, 31.13, 34.98, 36.79, 44.72, 52.25, 52.93, 62.12, 81.45, 88.43, 101.67, 104.53, 110.90, 119.12, 144.61, 156.57, 160.02.

Synthesis of 5-(Dihydroxyartemisinin-methyl)-furan-2-carbohydrazide (DHA-Furan-NH$_2$)

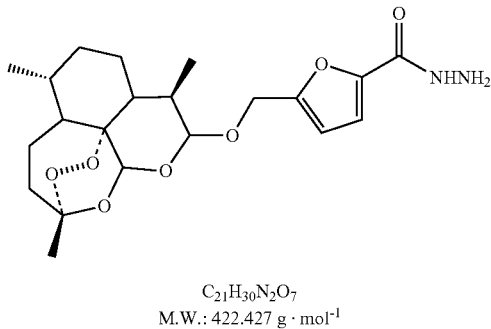

$C_{21}H_{30}N_2O_7$
M.W.: 422.427 g · mol$^{-1}$

DHA-furan-OMe (40 mg, 95 μmoles) and methanol (5 mL). were added to a 10 mL round bottom flask with a condenser, that was previously flame-dried under vacuum and flushed with nitrogen gas. The system was under nitrogen pressure. Anhydrous hydrazine (40 μL, 1.3 mmoles) was added and the reaction mixture heated at reflux for 24 h. After evaporation under vacuum, the compound was purified by silica gel column chromatography (11×2 cm). Samples (8 mL) were collected and the column covered with aluminum foil. Elution solvents were 50 mL 99:1 Chloroform/Methanol, 50 mL 97:3, 50 mL 95:5. The reaction was monitored by TLC and the TLC products stained with ninhydrin in EtOH. A yellow powder was obtained (25 mg, 63%). $^1$H-NMR ($C_6D_6$) δ 0.81 (m, 7H), 1.18 (m, 2H), 1.44 (m, 2H), 1.53 (brs, 1H), 1.57 (brs, 2H), 1.68 (m, 3H), 1.85 (m, 3H), 2.47 (dt, 1H), 2.87 (m, 1H) 3.95 (brs, 2H, exchangeable with $D_2O$), 4.48 (m, 3H), 4.88 (d, J=3.0 Hz, 1H), 5.62 (brs, 1H), 6.04 (m, 1H), 7.15 (d, J=2.4 Hz, 1H), 8.2 (brs, 1H, exchangeable with $D_2O$); $^{13}$C-NMR($C_6D_6$) δ 12.72, 19.85, 20.17, 24.55, 24.97, 25.93, 30.93, 31.56, 34.30, 24.55, 36.48, 37.32, 44.50, 46.47, 52.50, 61.93, 80.67, 81.32, 87.88, 101.69, 104.21, 110.89, 114.85, 147.56, 153.90, 158.9.

Example 6

Synthesis of 1-(Dihydroxyartemisinin-ethyl)-1H-1,2,3-triazole-4-carbohydrazide (DHA-Triazole-NH$_2$)

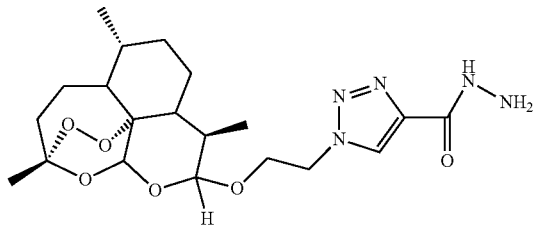

1-(Dihydroxyartemisinin-ethyl)-1H-1,2,3-triazole-4-carbohydrazide (DHA-Triazole-NH$_2$) was sequentially synthesized from 2-Azido ethanol: Methyl 1-(2-hydroxyethyl)-1H-1,2,3-triazole-4-carboxylate, Methyl 1-(Dihydroxyartemisinin-ethyl)-1H-1,2,3-triazole-4-carboxylate: DHA-Triazole-Ester, as shown below.

2-Azido ethanol

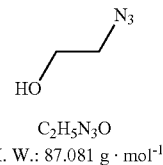

$C_2H_5N_3O$
M. W.: 87.081 g · mol$^{-1}$

2-Azido ethanol (Synthesis 1996, 11, 1345-49) was prepared as described below. 2-chloroethanol (2 mL, 30 mmoles) was rapidly added to a round bottom flask with a condenser containing sodium azide (2.34 g, 36 mmoles). The reaction mixture was heated to 30° C. for 1 h, and then 70° C. for 24 h. After a slow cool down to room temperature, the solution was extracted with diethylether. The organic phase was dried over $MgSO_4$ and the solvent evaporated to provide a colorless oil (1.882 g, 75%, d=1.149) and stored at 4° C. (slow decomposition was noted when stored at room temperature.). IR (DCM) cm$^{-1}$: 2125 $N_3$. NMR $^1$H 300 MHz, $CHCl_3$, (δ, ppm): 3.73 (m, 2H, $CH_2$OH), 3.38 (m, 2H $CH_2$N), 2.95 (b, 1H OH).

Methyl 1-(2-hydroxyethyl)-1H-1,2,3-triazole-4-carboxylate

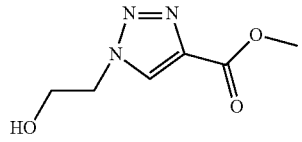

$C_6H_9N_3O_3$
M. W.: 171.154 g · mol$^{-1}$

Methyl 1-(2-hydroxyethyl)-1H-1,2,3-triazole-4-carboxylate (Tsypin, G. I.; Timofeeva, T. N., Mel'nikov, V. V.; Gidaspov, B. V. *Zh. Org. Khim.*, 1977, 13, 2275-2281) was synthesized as follows:

Azidoethanol (1 mL, 13.2 mmoles) and methylpropiolate (5 mL, 56.25 mmoles) were added to a 50 mL round bottom flask and mixed for 4 days at room temperature. A beige powder was obtained after drying under vacuum (2.43 g, quant.). NMR 1H 300 MHz, CHCl$_3$, (δ, ppm): 8.21 (s, 1H), 4.52 (t, J=4.8 Hz, 2H, CH$_2$N), 4.08 (q, J=1.8 Hz and 4.2 Hz, 2H, CH$_2$OH), 3.89 (s, 3H).

Methyl 1-(Dihydroxyartemisinin-ethyl)-1H-1,2,3-triazole-4-carboxylate (DHA-Triazole-Ester)

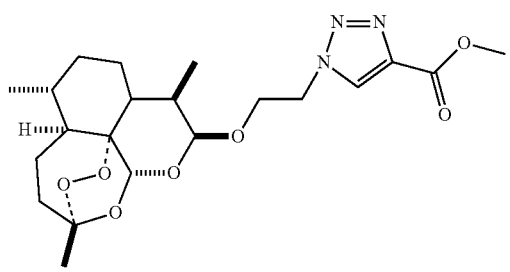

$C_{21}H_{31}N_3O_7$
M. W.: 437.487 g·mol$^{-1}$

Acetyl-dihydroxyartemisinin (50 mg, 0.154 mmole) in dry chloroform (0.5 mL) and the linker (32 mg, 0.187 mmole) were placed in a 2 mL round bottom flask that was previously flame-dried and flushed with nitrogen gas. The flask was placed in an ice-water bath and chloro trimethylsilane (25 μL, 0.197 mmole) was added dropwise. The reaction was maintained at 0° C. for 1 h, allowed to reach room temperature, and the flask was covered with aluminum foil. After 24 h, 0.5 mL of saturated sodium acetate was added. The organic phase was recovered and the aqueous phase extracted 2 times with chloroform. The organic phase was washed with brine and dried over Na$_2$SO$_4$ before the solvents were removed under vacuum. The crude product was purified by silica gel chromatography (1×3 cm) with 40 mL 7:3 Hexanes/AcOEt, which yielded a white powder after extracting oil product with diethyl ether (65 mg, 97%). NMR $^1$H 300 MHz, CDCl$_3$ (δ, ppm): 8.14 (s, 1H), 5.10 (s, 1H), 4.76 (d, J=3.3 Hz, 1H), 4.62 (m, 1H), 4.30 (m, 1H), 3.93 (s, 3H), 3.79 (m, 1H), 2.60 (m, 1H), 2.32 (m, 1H), 2.10-1.90 (m, 1H), 1.89-1.80 (m, 1H), 1.70-1.15 (m, 8H), 0.99-0.79 (m, 7H). NMR $^{13}$C 75.45 MHz, CDCl$_3$ (δ, ppm): 161.0, 139.5, 128.3, 104.2, 102.2, 87.8, 80.7, 66.1, 52.4, 52.2, 50.7, 44.0, 37.3, 36.3, 34.4, 30.6, 26.0, 24.6, 24.4, 20.3, 12.8.

1-(Dihydroxyartemisinin-ethyl)-1H-1,2,3-triazole-4-carbohydrazide (DHA-Triazole-NH$_2$)

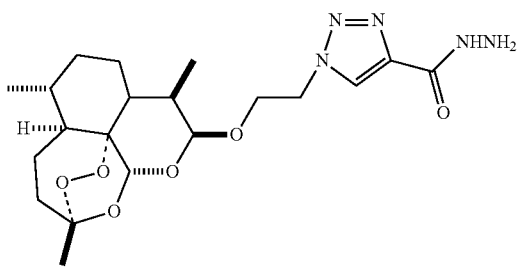

$C_{20}H_{31}N_5O_6$
M. W.: 437.49 g·mol$^{-1}$

The ester (DHA-Triazole-Ester) (15 mg, 34.3 μmoles), hydrazine hydrate (15 μL, 309 μmoles), and dry ethanol (0.5 mL) were placed in to a 5 mL round bottom flask that was previously flame dried and flushed with nitrogen. The flask was protected from light and the mixture stirred for 48 h at r.t. The solvent was evaporated and the product purified by silica gel chromatography (1×5 cm), eluting with 98:2 chloroform/ methanol, to yield a white powder (15 mg, Quant.). NMR $^1$H 300 MHz, CDCl$_3$ (δ, ppm): 8.28 (b, 1H), 8.11 (s, 1H), 5.11, (s, 1H), 4.75 (d, J=3.3 Hz, 1H), 4.64-4.59 (m, 2H), 4.35-4.28 (m, 1H), 4.04 (b, 1H), 3.83-3.76 (m, 1H), 2.62-2.57 (m, 1H), 2.32 (td, J=14.5 Hz and 3.9 Hz, 1H), 2.02-1.98 (m, 1H), 1.88-1.82 (m, 1H), 1.63-1.53 (m, 2H), 1.45-1.34 (m, 7H), 1.23-1.17 (m, 2H), 0.93-0.86 (m, 4H), 0.82-0.75 (m, 3H). NMR $^{13}$C 75.5 MHz, CDCl$_3$ (δ, ppm): 160.6, 141.7, 126.2, 104.2, 103.1, 102.0, 87.8, 65.9, 52.3, 50.7, 43.9, 37.3, 36.3, 34.3, 30.6, 26.0, 24.6, 24.3, 20.2, 12.8. ESI-MS positive (MeOH): 476.4 [M+K]$^+$, 460.4 [M+Na]$^+$ (100%), 438.4 [M+H]$^+$.

Example 7

Synthesis of aminoxy-artemisinin

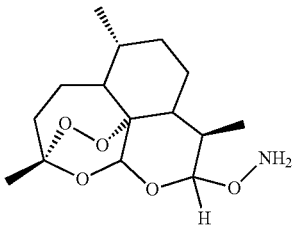

This compound was prepared from dihydroartemisinin by the published procedure (Kim and Sasaki, J. Org. Chem. 2004, 69, 3242-3244). The aminoxy-artemisinin reacts with benzaldehyde to form the corresponding oxime readily (Kim and Sasaki, J. Org. Chem. 2004, 69, 3242-3244)

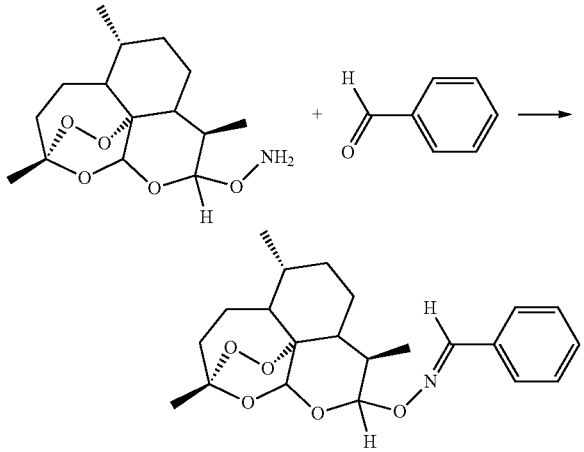

Example 8

Synthesis of Artelinic Acid Hydrazide

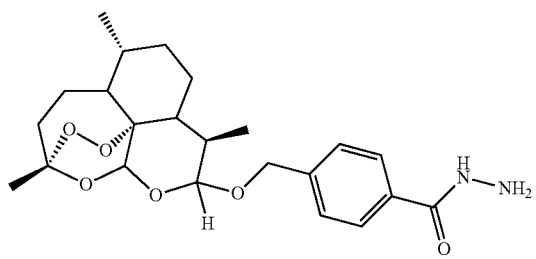 [SMILES: C[C@H]1C(OCc2ccc(C(=O)NN)cc2)OC2O[C@@]3(C)CCC4[C@H](C)CCC1[C@@]24OO3]

This compound was prepared from dihydroartemisinin by the published procedure (Lai et al., Life Science (2005), 76, 1267-1279).

Example 9

Synthesis of artemisinin-tagged HAIYPRH peptides

The following is an example of the synthesis of the artemisinin-tagged peptide HAIYPRH:

A solution of 4-formylbenzoyl-HAIYPRH (10 mg) in 1 mL of methanol-water (1:1) and a solution of artelinic acid hydrazine (5 mg) in 1 mL of methanol-water (1:1) were added to a 2 mL round bottom reaction vessel. The mixture was stirred for 1 hr. The solvent was removed by rotavap, and the residue purified by reverse phase HPLC. The same HPLC condition as that of Example 1 was used. The retention times were 18 min, 24 min and 29 min for 4-formylbenzoyl-HAIYPRH, artelinic acid hydrazine and the conjugate, respectively. The yield was 11 mg. Ion-spray MS: m/z=1438.7 (M+H)$^+$.

Example 10

Synthesis of Lysine-Branched Artemisinin-Tagged HAIYPRH Peptides

The following is an example of the synthesis of the lysine-branched artemisinin-tagged HAIYPRH peptide:

This compound was prepared by the same procedure as that for Example 9, except that 2 equivalents of artelinic acid hydrazide was used for conjugation. Ion-spray MS: m/z=2112.9 (M+H)$^+$.

Example 11

Synthesis of α,ε-(bis(4-formylbenzoyl)Lys)$_2$-Lys-His-Ala-Ile-Tyr-Pro-Arg-His-amide

HAIYPRH

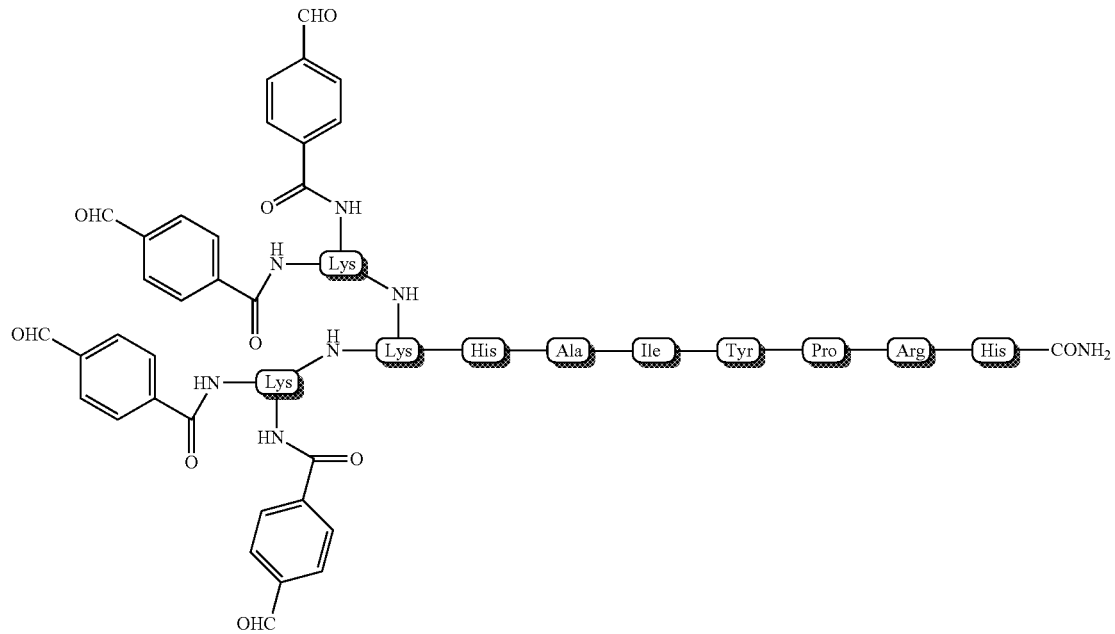

Fmoc-Rink resin (0.5 gram) was placed in a 10 mL reaction vessel. Fmoc-Ala, Fmoc-Ile, Fmoc-Tyr(tBu), Fmoc-His(Trt), Fmoc-Arg(PMC), (Fmoc)$_2$-Lys and two equivalents of (Boc)$_2$-Lys were sequentially coupled to assemble the desired peptide on the resin. The final Fmoc group was then deprotected with 20% piperidine in DMF, and 4-formylbenzoic acid (4 equivalent) was coupled to the N-terminus Lys residues. The peptide was cleaved from resin in 5 mL of 20% TFA (trifluoroacetic acid) in CH$_2$Cl$_2$ for 15 min. The resin was removed by filtration, and washed with CH$_2$Cl$_2$ 3 times. The filtrate and washings were combined and concentrated to approximately 2 mL. Dry ether (30 ml) was added to the residue to precipitate the peptide. The precipitates were collected by centrifugation, and washed with ether 3 times. After vacuum drying, the crude product (0.3 gram) was obtained and purified by reverse phase HPLC. The C4 reverse-phase column was used with a linear gradient from 100% water (0.1% TFA) to 60% acetonitrile-40% water (0.1% TFA). The peptide was detected by the absorbance at 270 nm. The yield was 0.1 gram. Ion Spray MS: m/z=1804.7 (M+H)$^+$, 1826.7 (M+Na)$^+$

Example 12

Synthesis of Lysine-Branched Artemisinin-Tagged HAIYPRH Peptides

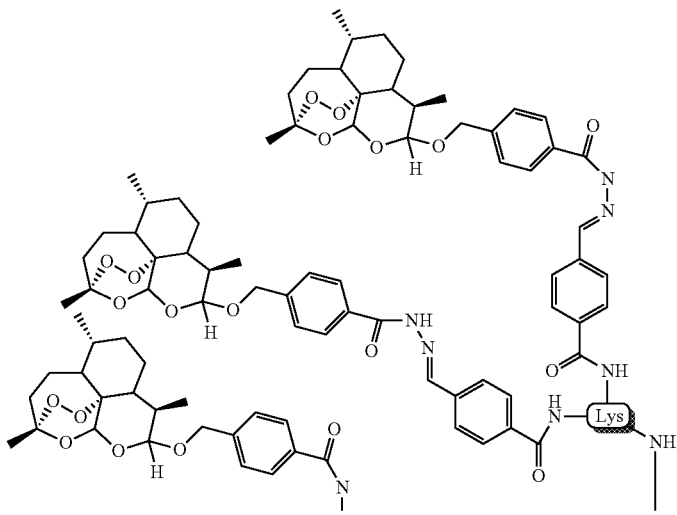

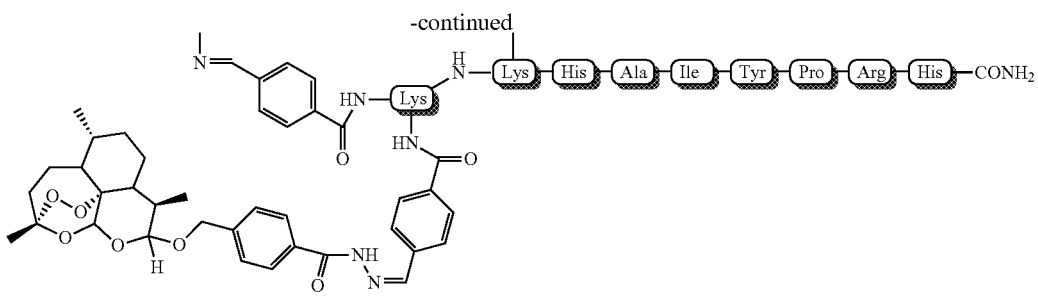

The compound was prepared by the same procedure as that for EXAMPLE 9, except that 4 equivalents of artelinic acid hydrazide was used for conjugation. Ion-spray MS: m/z=3461.7 (M+H)$^+$, 3483.7 (M+Na)$^+$.

Example 13

Synthesis of Trioxane Dimer Hydrazide

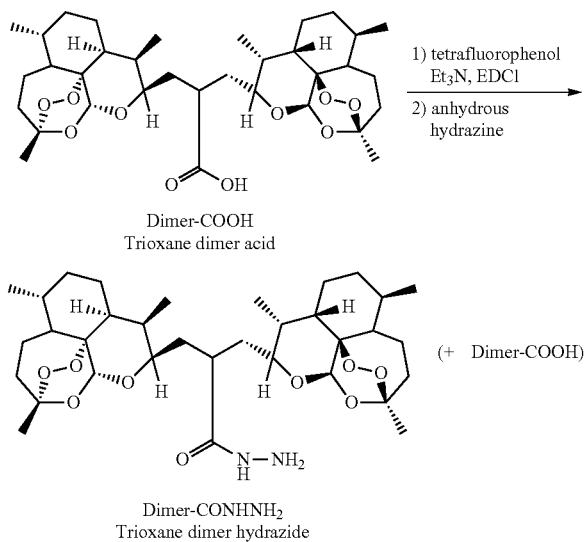

A solution of dimer-COOH (17 mg, 27 μmol) in a dried dichloromethane-DMSO (20:1=1 mL) was modified by addition of EDCI (12.4 mg, 65 μmol) and tetrafluorophenol (10.6 mg, 64 μmol) in the presence of Et$_3$N (20 μL). The reaction was stirred for 1 h at room temperature, the mixture then treated with an excess of anhydrous hydrazine (10 μL). The reaction was kept standing for 3 h. The product was purified by short silica gel column chromatography, and the product eluted with chloroform, followed by chloroform-methanol (20:1). The product-containing fractions were combined, and concentrated under reduced pressure to yield 13 mg of a mixture of dimer-COOH and the corresponding hydrazide (dimer-CONHNH$_2$). The ratio of the two trioxane dimers was determined to be 1:1, based on the integrals of $^1$H-NMR of the reaction product. 300 MHz $^1$H NMR (CDCl$_3$) δ 7.03 (s, 1H), 5.30 (s, 1H), 5.17 (s, 1H), 4.20-4.05 (m, 2H), 1.43, (s), 1.39 (s), 0.93 (d, J=6.0, 6H), 0.84 (d, J=7.6, 6H); LRMS (ES) m/z=657.6 (M+Na$^+$)

Example 14

Figure 3A:
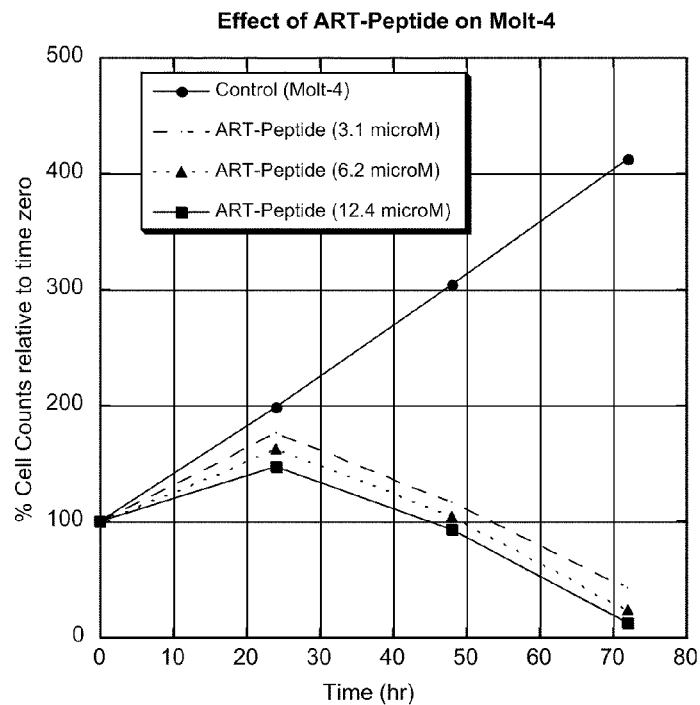
FIG. 3 shows the effect of artemisinin-tagged peptide HAIYPRH on cultured human Molt-4 lymphobastoid leukemia cells and normal human lymphocytes. Cell viability was determined at 24, 48, and 72 hours in the presence of different concentrations (3.1, 6.2, 12.4 µM) of artemisinin-tagged peptide. The artemisinin-tagged peptide killed Molt-4 cells very effectively at low micromolar concentrations without affecting normal lymphocytes (FIGS. 3A and 3B). The IC$_{50}$ values of ART-peptide and ART2-peptide on Molt-4 cells were 4.23±0.09 µM and 0.86±0.10 µM at 72 hrs, respectively (FIGS. 3C and 3D). ART-peptide and ART2-peptide were peptides covalently attached with one and two artemisinin moieties, respectively. The artemisinin-tagged peptides were virtually non-toxic to normal leukocytes (IC$_{50}$>10,000 uM, data not shown). Under the same assay condition, DHA showed IC$_{50}$ values of 5.3±0.26 µM and 43±22 µM for Molt-4 cells and normal leukocytes, respectively. Therefore, tagging to the TfR-binding peptide significantly improved the anti-cancer potency and selectivity of artemisinin. The in vitro cancer cytotoxicity of the artemisinin-tagged peptides is comparable to or higher than that of the other commonly used anti-cancer drugs, except that the artemisinin-tagged peptides show much higher cancer/normal cell selectivity.
FIGS. 3E and 3F show the effect of ART-peptide and ART2-peptide on medulloblastoma cells (DAOY cells). Both compounds are effective against this cell line, and it is clear that ART2-peptide is more effective than ART-peptide.

Toxicity of the Artemisinin-Tagged Peptide in Leukemia Cells and Normal Lymphocytes The artemisinin-tagged peptide HAIYPRH was tested on human Molt-4 lymphobastoid leukemia cells and compared with normal human lymphocytes, as follows. Molt-4 cells (obtained from the ATCC, Manassas, Va.) were cultured at 37° C. in 5% CO$_2$/95% air and 100% humidity in culture flasks. Cell viability was determined before an experiment by using trypan blue dye exclusion. After an initial counting of cells, human holotransferrin (Sigma Chemicals, St. Louis, Mo.) was added to samples of the cells. Different concentrations (3.1, 6.2, 12.4 μM) of 'artemisinin-tagged peptide' (dissolved in 0/1 mL of complete medium) were added 1 hr later to the cell samples. The final concentration of holotransferrin was 12 μM (which is the concentration in human circulation). An equal volume of medium was added to control samples. Cells were kept in an incubator at 37° C. under 5% CO$_2$/95% air and 100% humidity during the experiment. At 24, 48 and 72 hrs after the addition of the tagged peptide, cell concentrations in appropriate flasks were counted using a counting hemocytometer chamber and microscope. In a similar set up, the same procedures were carried out on normal human lymphocytes. The artemisinin-tagged peptide killed Molt-4 cells very effectively at low micromolar concentrations without affecting normal lymphocytes, as shown in FIGS. 3A and B, respectively.

Figure 3B:
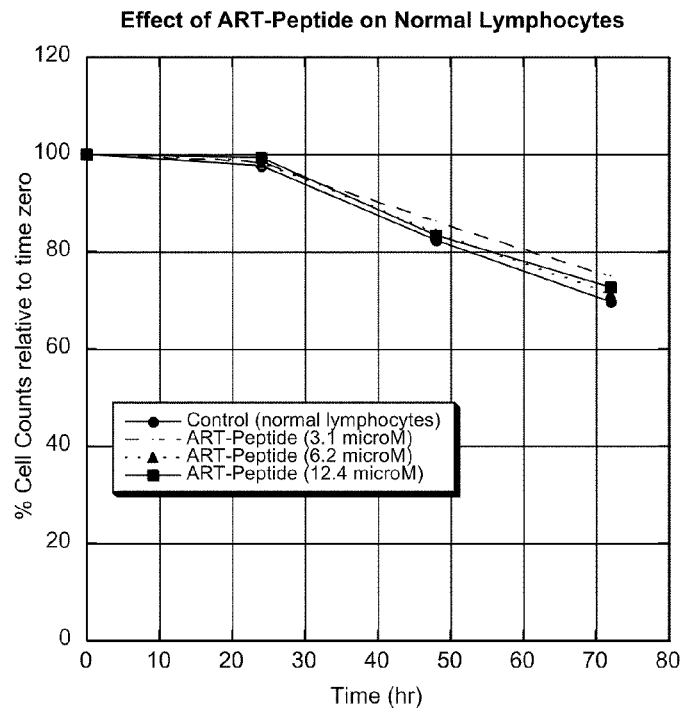
Figure 3C:
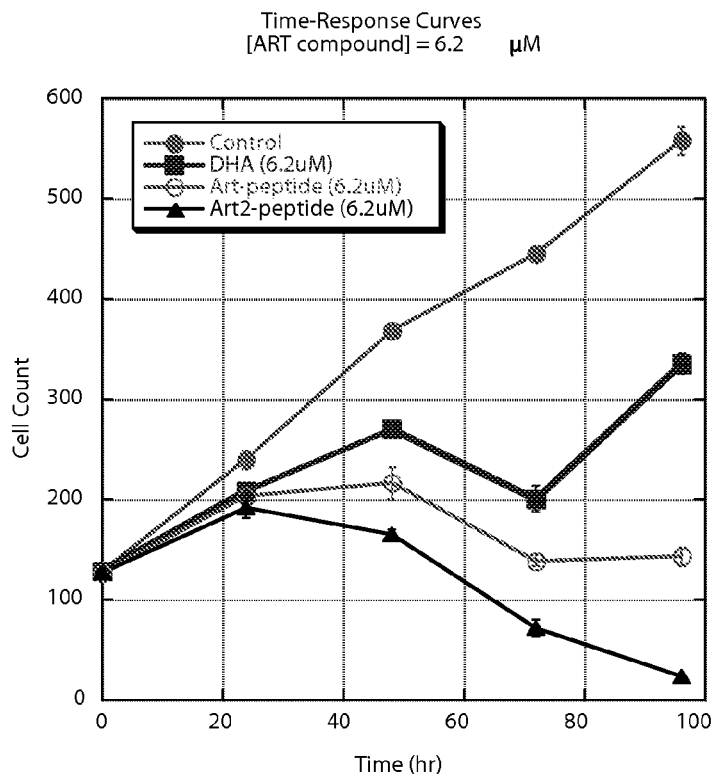
Figure 3D:
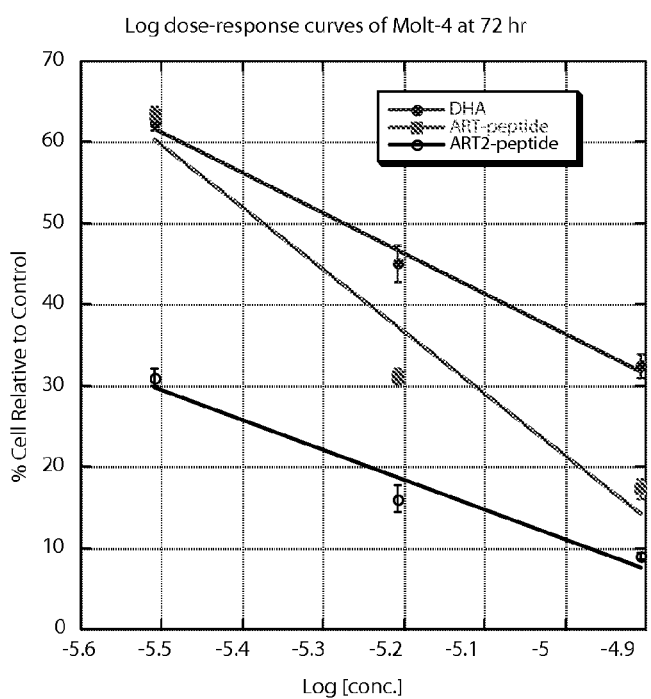

The IC$_{50}$ values of ART-peptide and ART2-peptide on Molt-4 cells were 4.23±0.09 μM and 0.86±0.10 μM at 72 hrs, respectively (FIGS. 3C and 3D). The artemisinin-tagged peptides were virtually non-toxic to normal leukocytes (IC$_{50}$>10,000 uM, FIG. 3B). Under the same assay condition, DHA showed IC$_{50}$ values of 5.3±0.26 uM and 43±22 μM for Molt-4 cells and normal leukocytes, respectively. Therefore, tagging to the TfR-binding peptide significantly improved the anticancer potency and selectivity of artemisinin. The in vitro cancer cytotoxicity of the artemisinin-tagged peptides is comparable to or higher than that of the other commonly used anti-cancer drugs, except that the artemisinin-tagged peptides show much higher cancer/normal cell selectivity. When both ART-peptide and ART2-peptide are kept in DMSO at room temperature for one month, essentially no change in activity was observed, except for ART-peptide that showed a significant increase in activity after the storage in DMSO, presumably due to its slow dissolution rate in DMSO.

TABLE 5

LD$_{50}$ of Selected compounds

| Compounds | LD$_{50}$ (μM)$^a$ (fresh sample) | LD$_{50}$ (μM)$^a$ (after stored in DMSO at room temperature for 30 days) |
|---|---|---|
| DHA | 5.3 ± 0.26 | 5.01 ± 0.35 |
| Art-peptide$^B$ | 4.23 ± 0.09 | 1.06 ± 0.08 |
| Art$_2$-peptide$^B$ | 0.86 ± 0.1 | 0.61 ± 0.05 |

$^a$after 72 hr
$^b$all the cells are dead after 7 days

Example 15

Inhibition of Growth of Rat Breast Cancer Cells

The artemisinin-tagged peptide HAIYPRH was also tested on rat breast cancer cells, as follows. MTLn3 rat breast cancer cells were grown in complete MEM from GIBCO/BRL (Rockville, Md.) at 37° C. in a humid atmosphere containing 5% CO$_2$. After confluency, the cells were trypsinized and plated in a ratio of 1:4 to a T-25 flask. Testing was done on cultures at 24 hrs after plating. The cells were counted in one set of flasks. Each flask contained approximately one hundred thousand cells. Medium from cultures was aspirated and 5 ml each of the same medium containing 12.4 μM of the tagged peptide was added to each flask. The cells were incubated for 72 hrs at 37° C.

Since this is a test to investigate whether the artemisinin-tagged peptide also kills rat cancer cells, only one drug concentration and one test time point were studied. Medium from a flask was aspirated out and collect in a 50 ml tube. Attached cells were washed twice with 5 ml of PBS (phosphate buffered saline without calcium and magnesium) each time and these washes were collected along with the medium. Two milliliters of freshly made 0.025% trypsin (Amresco, Solan, Ohio) in PBS at 37° C. were then added for 5 min to detach cells from the flask. Detached cells were collected along with the medium and washes from the flask. Thus, all cells floating as well as detached using trypsin, were collected together. Ten microliters of this cell suspension were loaded on each side of a hemocytometer and all cells (normal, as well apoptotic and necrotic) were counted. Apoptotic and necrotic cells were identified using the morphological criteria. Controls were cells subjected to the same protocol, but not treated with the 'tagged-peptide'. The data show that at 72 hrs after the above treatment, the artemisinin-tagged peptide (at 12.4 μM) retarded the growth of the rat breast cancer cells by approximately 40%. The surviving cells were not able to attach to the culture plate, indicating that the peptide binds to rat transferrin receptors as well as human transferrin receptors.

Example 16

Inhibition of Growth of Medulloblastoma Cancer Cells

Figure 3E:
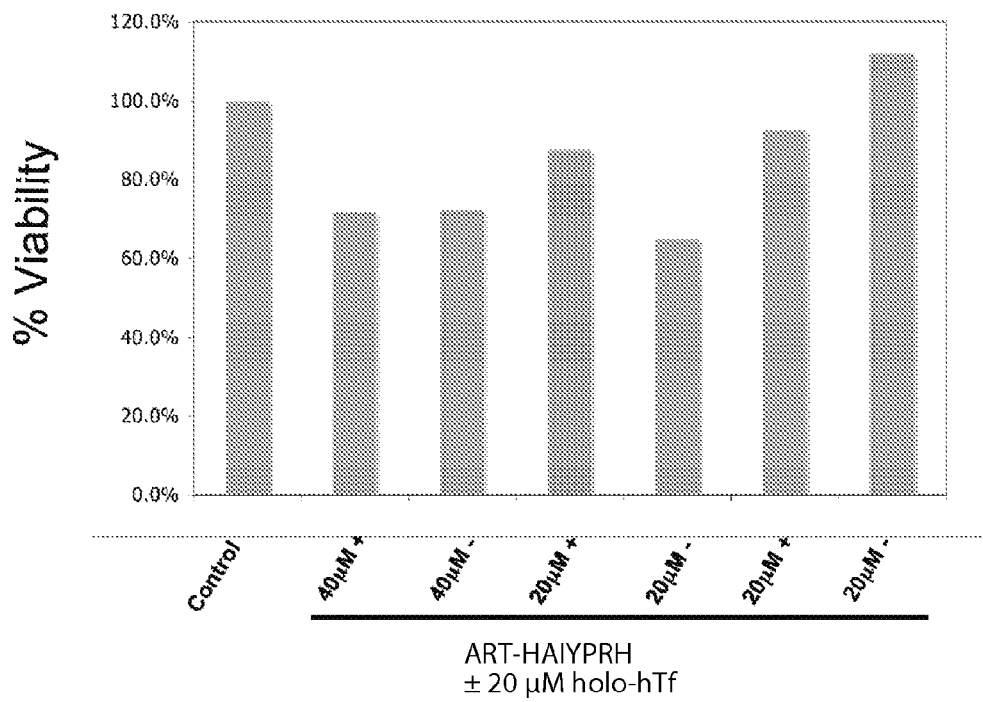
Figure 3F:
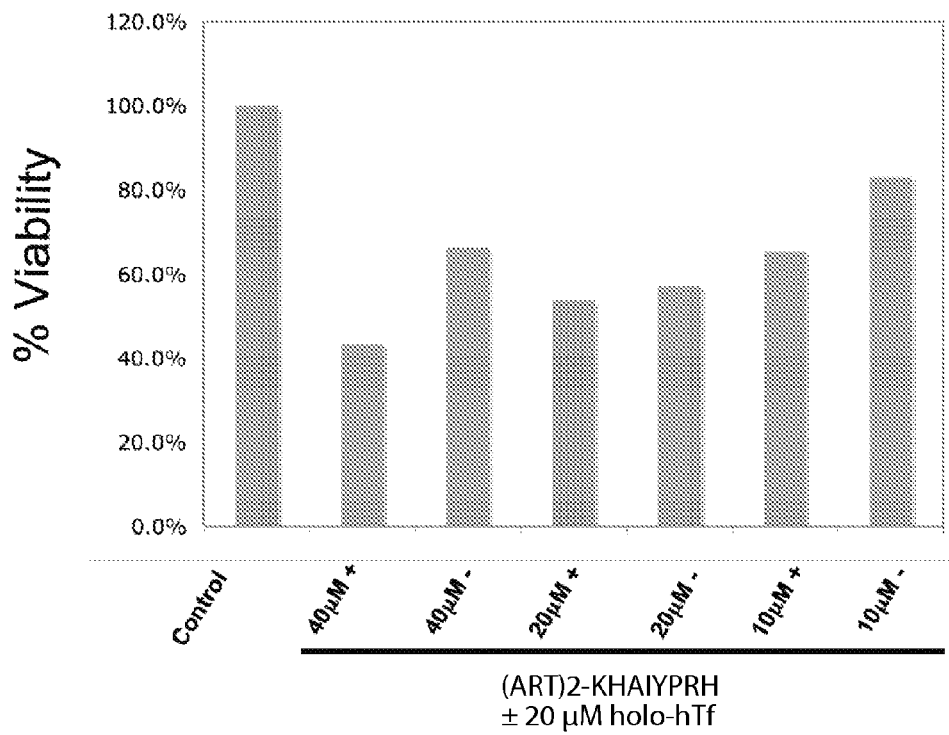

DAOY human Medulloblastoma cells (10,000 cells/200 μL) were seeded on a 96 well plate and incubated for 24 h at 37° C. Cell culture medium was removed after 24 h and 150 μL of medium with different combinations of drug treatment was added. Human holotransferrin (20 μM) was added to half of the samples. Treatment medium was removed after 48 h, and 100 μL of cell medium was added, and the following protocol was used to determine cell viability: (1) 10 μL of 12 mM MTT reagent was added to each well; (2) the cultures were incubated at 37° C. for 4 h; (3) 100 μL of isopropanol was added to each well to lyse the cells and then incubated at 4° C. for 30 min; (4) after incubation each well was plunged (3×200 μL) to ensure the cells were lysed; (5) the samples were then centrifuged at 13,000 rpm in a microcentrifuge for 3 min at room temperature; and (6) 100 μL of the supernatant was read in a plate reader at λ=570 nm. FIGS. 3E and 3F show the effects of peptides tagged with one and two moieties of artemisinin, respectively. Both peptides inhibited the growth of human medulloblastoma cells in vitro. In addition, peptide containing two artemisinin moieties is more potent than peptide containing one moiety.

Example 17

Inhibition of Rat Breast Tumor Growth In Vivo

Figure 4:
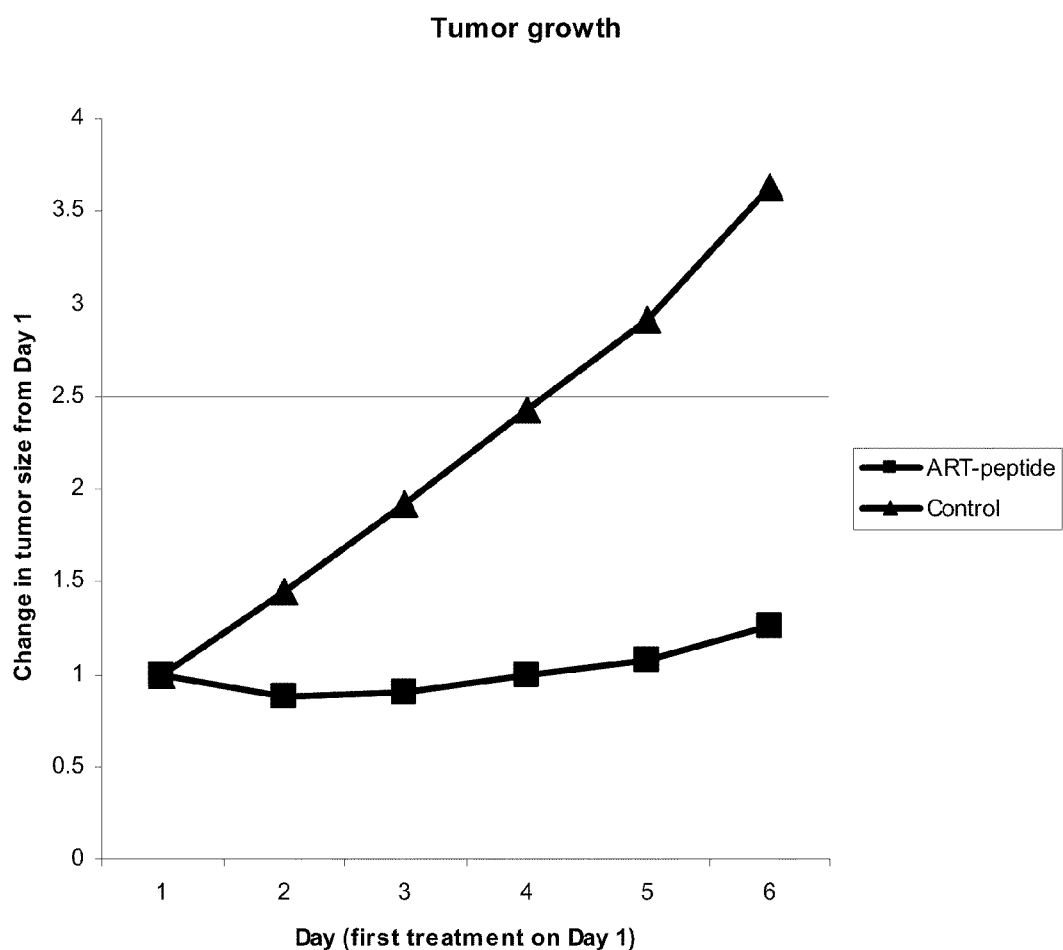
FIG. 4 shows the effect of artemisinin-tagged peptide HAIYPRH on breast tumors in an in vivo cancer model. Rats with breast tumors that were previously induced by injections with MTLn3 breast cancer cells and between 5 mm to 10 mm in diameter were treated daily with the artemisinin-tagged peptide for 5 days. The artemisinin-tagged peptide was dissolved in a phosphate buffer at pH 7.4. 0.1 mL of the buffer containing 0.5 mg of the tagged-peptide was injected daily via a tail vein. Controls were injected with 0.1 mL of the buffer daily. The length, width, and height of ellipsoidal tumor were measured with a caliper. The tumor volume was calculated using the formula: length×width×height×π/6. The results presented in the figure are expressed as percent change in tumor volume from the first day of tagged-peptide treatment for each rat. Intravenous injection of the peptide significantly retarded the growth of breast tumors in the rat.

The artemisinin-tagged peptide HAIYPRH was then tested in an animal cancer in vivo model. In this experiment, breast tumors were induced in rats by injecting subcutaneously 1 million rat MTLn3 breast cancer cells. When the tumors had reached a size between 5 mm to 10 mm in diameter, rats were treated daily with the tagged peptide for 5 days, as follows. The artemisinin-tagged peptide was dissolved in a phosphate buffer at pH 7.4. 0.1 mL of the buffer containing 0.5 mg of the tagged-peptide was injected daily via a tail vein. Controls were injected with 0.1 mL of the buffer daily. The length, width, and height of each ellipsoidal tumor were measured with a caliper. The tumor volume was calculated using the formula: length×width×height×π/6. The results are shown in FIG. 4, where the data were expressed as percent change in tumor volume from the first day of tagged-peptide treatment for each rat. Intravenous injection of the peptide significantly retarded the growth of breast tumors in the rat.

While the preferred embodiment of the invention has been illustrated and described, it will be appreciated that various changes can be made therein without departing from the spirit and scope of the invention. All references, patents, or applications cited herein are incorporated by reference in their entirety, as if written herein.

---

The embodiments of the invention in which an exclusive property or privilege is claimed are defined as follows:

1. A conjugate comprising at least one endoperoxide covalently linked to the peptide having the sequence of SEQ ID NO: 1 or SEQ ID NO: 2, wherein the endoperoxide has the structure:

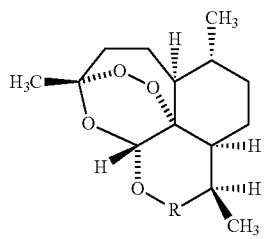

wherein R is —(C=O)— or —CH($R_1$)—, where $R_1$ is selected from the group consisting of hydrogen, hydroxyl, alkyl, —$OR_2$, —(C=O)$R_2$, —(C=O)$OR_2$, —(C=O)($CH_2$)$_n$(C=O)OH, and —S(C=O)$OR_2$, where $R_2$ is alkyl or aryl and n is 1 to 6.

2. The conjugate of claim 1, wherein the conjugate comprises two endoperoxides.

3. The conjugate of claim 1, wherein the conjugate has the following formula:

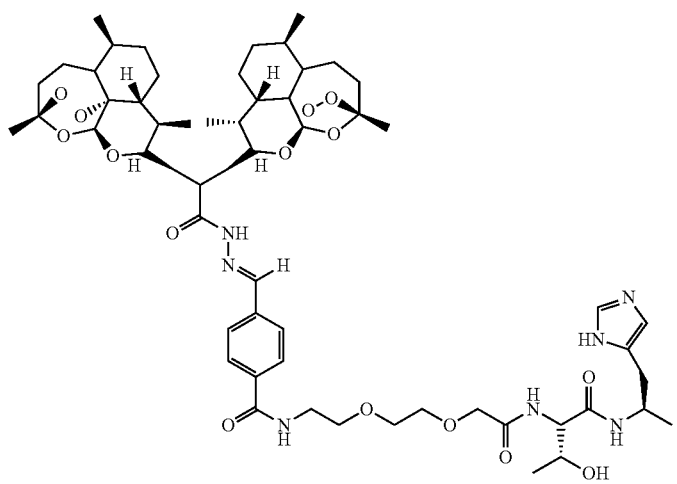

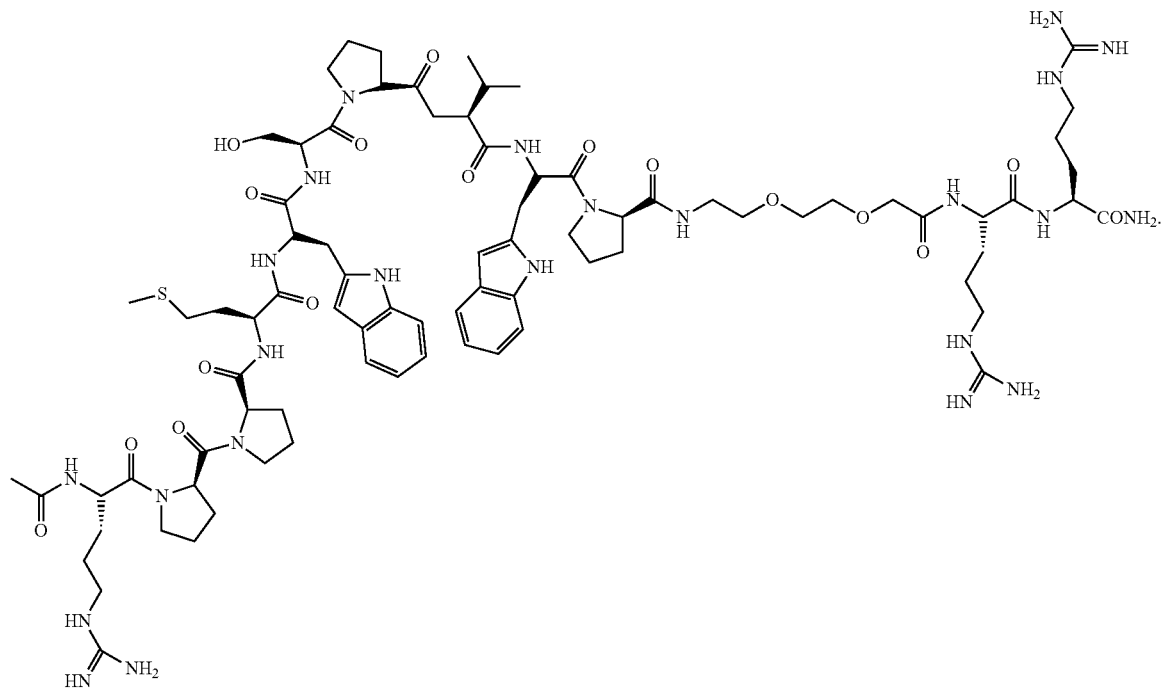
4. The conjugate of claim 1, wherein the conjugate has the following formula:
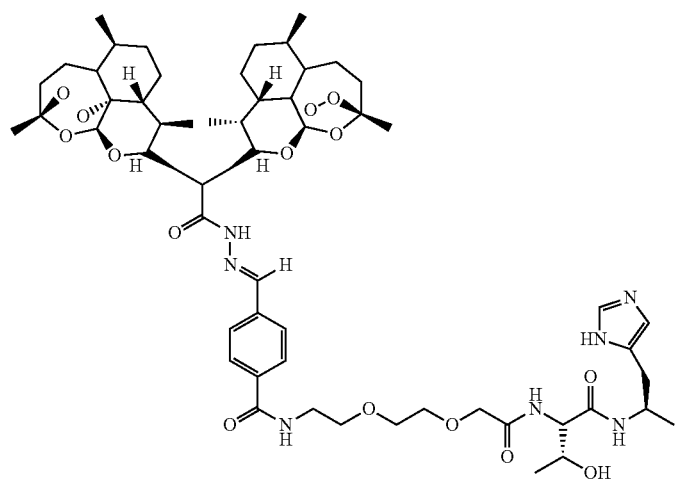

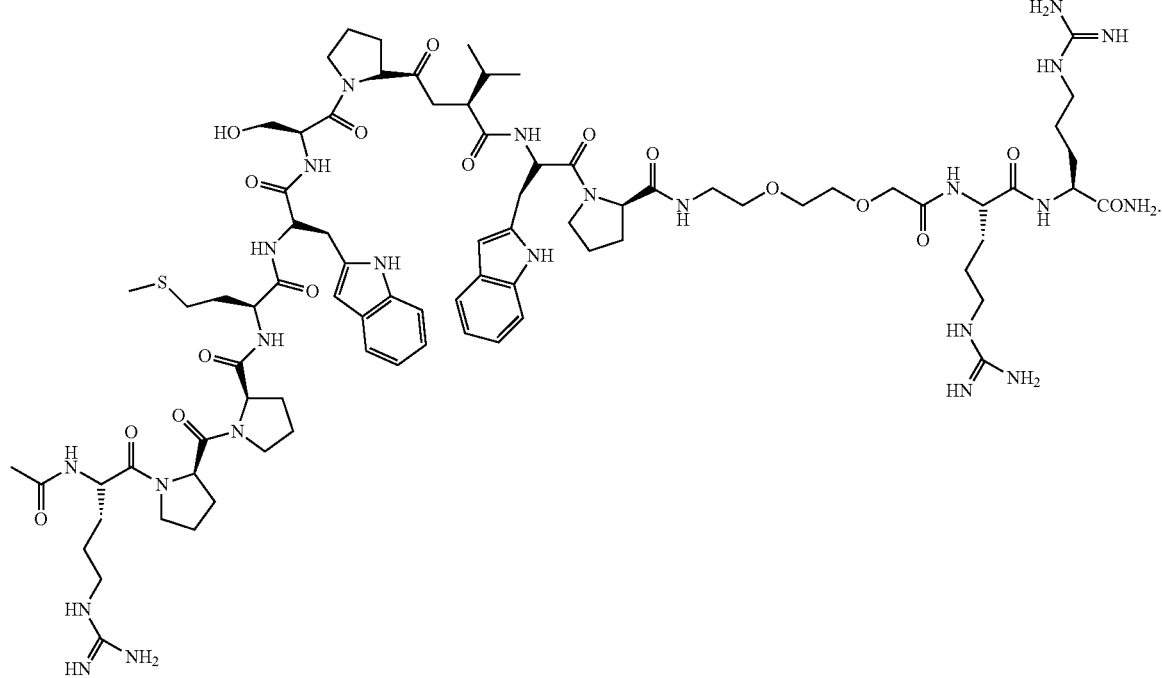
5. A composition comprising the conjugate of claim 1 and a pharmaceutically acceptable carrier.
* * * * *

SEQUENCE LISTING

<160> NUMBER OF SEQ ID NOS: 2

<210> SEQ ID NO 1
<211> LENGTH: 7
<212> TYPE: PRT
<213> ORGANISM: Artificial
<220> FEATURE:
<223> OTHER INFORMATION: Synthetic Peptide

<400> SEQUENCE: 1

His Ala Ile Tyr Pro Arg His
1               5

<210> SEQ ID NO 2
<211> LENGTH: 12
<212> TYPE: PRT
<213> ORGANISM: Artificial
<220> FEATURE:
<223> OTHER INFORMATION: Synthetic Peptide

<400> SEQUENCE: 2

Thr His Arg Pro Pro Met Trp Ser Pro Val Trp Pro
1               5                   10